(12) United States Patent
Dorian et al.

(10) Patent No.: US 8,105,495 B2
(45) Date of Patent: *Jan. 31, 2012

(54) METHOD FOR PREPARING PLATELET RICH PLASMA AND CONCENTRATES THEREOF

(75) Inventors: Randel Dorian, San Diego, CA (US); Michael D. Leach, Warsaw, IN (US)

(73) Assignees: Hanuman, LLC, San Francisco, CA (US); Biomet Biologics, LLC, Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/987,605

(22) Filed: Jan. 10, 2011

(65) Prior Publication Data

US 2011/0100919 A1 May 5, 2011

Related U.S. Application Data

(60) Division of application No. 11/831,605, filed on Jul. 31, 2007, now Pat. No. 7,866,485, which is a continuation-in-part of application No. 11/342,749, filed on Jan. 30, 2006, now Pat. No. 7,824,559.

(60) Provisional application No. 60/723,312, filed on Oct. 4, 2005, provisional application No. 60/654,718, filed on Feb. 17, 2005, provisional application No. 60/651,050, filed on Feb. 7, 2005, provisional application No. 60/834,550, filed on Jul. 31, 2006.

(51) Int. Cl.
| | |
|---|---|
| *B01D 21/26* | (2006.01) |
| *B01D 15/00* | (2006.01) |
| *B01D 33/00* | (2006.01) |
| *B01D 35/00* | (2006.01) |
| *B01D 37/00* | (2006.01) |
| *B04B 3/00* | (2006.01) |
| *B04B 1/04* | (2006.01) |

(52) U.S. Cl. ........ 210/782; 210/767; 210/784; 210/787; 210/789; 494/2; 494/4; 494/36; 494/37; 494/43; 494/54; 494/67; 494/74; 494/79

(58) Field of Classification Search ............... 210/360.1, 210/767, 781, 782, 784, 787, 789; 494/2, 494/4, 36, 37, 43, 54, 67, 74, 79

See application file for complete search history.

(56) References Cited

U.S. PATENT DOCUMENTS 3,141,846 A 7/1964 Laven, Jr.
(Continued)

FOREIGN PATENT DOCUMENTS

AU 42863/96 1/1999
(Continued)

OTHER PUBLICATIONS

"Cell Isolation Techniques, Methods and Materials, Working with Enzymes," (2004) (9 pages) Worthington Biochemical Corp.

(Continued)

*Primary Examiner* — John Kim
(74) *Attorney, Agent, or Firm* — Harness, Dickey

(57) ABSTRACT

A process for separating platelet rich plasma from a blood sample using a platelet rich plasma separator system is disclosed. The system includes an inner wall having a top edge and a central axis that is surrounded by a depth filter having a capacity to receive all of the erythrocytes in the blood sample, where an inner surface of the inner wall has an angle of about 0.2° from the central axis of the inner wall. The process includes spinning the inner cylinder at its central axis at a speed that separates the erythrocytes from plasma and platelets and causes the erythrocytes to collect against an inner surface of the depth filter. The cylinder is continually spun for a sufficient time to allow substantially all of the erythrocytes to flow up the inner surface and over the top edge into the depth filter, leaving platelet enriched plasma (PRP) in the inner cylinder, such that upon discontinuing the spinning, permits the platelet enriched plasma to flow to the bottom of the inner cylinder.

22 Claims, 23 Drawing Sheets

U.S. PATENT DOCUMENTS

| | | |
|---|---|---|
| 3,409,165 A | 11/1968 | Creith |
| 3,420,374 A | 1/1969 | Umeda |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,593,915 A | 7/1971 | Steinacker |
| 3,647,070 A | 3/1972 | Adler |
| 3,779,383 A | 12/1973 | Ayres |
| 3,785,549 A | 1/1974 | Latham, Jr. |
| 3,814,248 A | 6/1974 | Lawhead |
| 3,850,369 A | 11/1974 | Bull et al. |
| 3,879,295 A | 4/1975 | Glover et al. |
| 3,894,952 A | 7/1975 | Ayres |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,941,699 A | 3/1976 | Ayres |
| 3,972,812 A | 8/1976 | Gresl, Jr. |
| 3,982,691 A | 9/1976 | Schlutz |
| 4,001,122 A | 1/1977 | Griffin |
| 4,046,699 A | 9/1977 | Zine, Jr. |
| 4,055,501 A | 10/1977 | Cornell |
| 4,059,108 A | 11/1977 | Latham, Jr. |
| 4,077,396 A | 3/1978 | Wardlaw et al. |
| 4,152,270 A | 5/1979 | Cornell |
| 4,159,896 A | 7/1979 | Levine et al. |
| 4,187,979 A | 2/1980 | Cullis et al. |
| 4,204,537 A | 5/1980 | Latham, Jr. |
| 4,225,580 A | 9/1980 | Rothman et al. |
| 4,229,298 A | 10/1980 | Bange |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. et al. |
| 4,322,298 A | 3/1982 | Persidsky |
| 4,332,351 A | 6/1982 | Kellogg et al. |
| 4,362,567 A | 12/1982 | Schwarz et al. |
| 4,364,832 A | 12/1982 | Ballies et al. |
| 4,377,572 A | 3/1983 | Schwarz et al. |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi et al. |
| 4,427,650 A | 1/1984 | Stroetmann et al. |
| 4,427,651 A | 1/1984 | Stroetmann et al. |
| 4,442,655 A | 4/1984 | Stroetmann et al. |
| 4,446,021 A | 5/1984 | Aufderhaar et al. |
| 4,453,939 A | 6/1984 | Zimmerman et al. |
| 4,464,167 A | 8/1984 | Schoendorfer et al. |
| 4,537,767 A | 8/1985 | Rothman et al. |
| RE32,089 E | 3/1986 | Blatt et al. |
| 4,610,656 A | 9/1986 | Mortensen |
| 4,617,009 A | 10/1986 | Ohlin et al. |
| 4,627,879 A | 12/1986 | Rose et al. |
| 4,631,055 A | 12/1986 | Redl et al. |
| 4,632,761 A | 12/1986 | Bowers et al. |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger et al. |
| 4,714,457 A | 12/1987 | Alterbaum |
| 4,722,790 A | 2/1988 | Cawley et al. |
| 4,724,317 A | 2/1988 | Brown et al. |
| 4,735,616 A | 4/1988 | Eibl et al. |
| 4,735,726 A | 4/1988 | Duggins |
| 4,738,655 A | 4/1988 | Brimhall et al. |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers et al. |
| 4,834,890 A | 5/1989 | Brown et al. |
| 4,839,058 A | 6/1989 | Cawley et al. |
| 4,844,818 A | 7/1989 | Smith |
| 4,846,780 A | 7/1989 | Galloway et al. |
| 4,846,974 A | 7/1989 | Kelley et al. |
| 4,853,137 A | 8/1989 | Ersson et al. |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani et al. |
| 4,900,453 A | 2/1990 | Sedlmayer et al. |
| 4,902,281 A | 2/1990 | Avoy |
| 4,928,603 A | 5/1990 | Rose et al. |
| 4,929,242 A | 5/1990 | Desecki et al. |
| 4,933,291 A | 6/1990 | Daiss et al. |
| 4,943,273 A | 7/1990 | Pages et al. |
| 4,946,601 A | 8/1990 | Fiehler |
| 4,950,220 A | 8/1990 | Wells et al. |
| 4,957,638 A | 9/1990 | Smith |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |
| 5,030,215 A | 7/1991 | Morse et al. |
| 5,030,341 A | 7/1991 | McEwen et al. |
| 5,045,048 A | 9/1991 | Kaleskas et al. |
| 5,053,127 A | 10/1991 | Schoendorfer et al. |
| 5,071,570 A | 12/1991 | Shiraki et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson et al. |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling et al. |
| 5,185,001 A | 2/1993 | Galanakis |
| 5,188,583 A | 2/1993 | Guigan et al. |
| 5,190,057 A | 3/1993 | Sarfarazi |
| 5,190,759 A | 3/1993 | Lindblad et al. |
| 5,204,537 A | 4/1993 | Bennet et al. |
| 5,206,023 A | 4/1993 | Hunziker et al. |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,234,608 A | 8/1993 | Duff |
| 5,236,604 A | 8/1993 | Fiehler |
| 5,258,126 A | 11/1993 | Pall et al. |
| 5,260,420 A | 11/1993 | Burnouf-Radosevich et al. |
| 5,269,927 A | 12/1993 | Fiehler |
| 5,271,852 A | 12/1993 | Luoma, II |
| 5,279,825 A | 1/1994 | Wehling et al. |
| 5,281,342 A | 1/1994 | Biesel et al. |
| 5,290,552 A | 3/1994 | Sierra et al. |
| 5,290,918 A | 3/1994 | Bui-Khac et al. |
| 5,298,171 A | 3/1994 | Biesel et al. |
| 5,304,372 A | 4/1994 | Michalski et al. |
| 5,316,674 A | 5/1994 | Pall et al. |
| 5,318,524 A | 6/1994 | Morse et al. |
| 5,318,782 A | 6/1994 | Weis-Fogh et al. |
| 5,321,126 A | 6/1994 | van Dommelen et al. |
| 5,322,620 A | 6/1994 | Brown et al. |
| 5,330,974 A | 7/1994 | Pines et al. |
| 5,344,752 A | 9/1994 | Murphy |
| 5,370,802 A | 12/1994 | Brown |
| 5,376,263 A | 12/1994 | Fischel |
| 5,387,187 A | 2/1995 | Fell et al. |

| | | |
|---|---|---|
| 5,393,674 A | 2/1995 | Levine et al. |
| 5,395,923 A | 3/1995 | Bui-Khac et al. |
| 5,403,272 A | 4/1995 | Deniega et al. |
| 5,405,607 A | 4/1995 | Epstein |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,480,378 A | 1/1996 | Weis-Fogh et al. |
| 5,484,383 A | 1/1996 | Fitch, Jr. et al. |
| 5,494,578 A | 2/1996 | Brown et al. |
| 5,494,592 A | 2/1996 | Latham, Jr. et al. |
| 5,505,685 A | 4/1996 | Antwiler |
| 5,510,102 A | 4/1996 | Cochrum |
| 5,533,518 A | 7/1996 | Vogler |
| 5,560,830 A | 10/1996 | Coleman et al. |
| 5,577,513 A | 11/1996 | Van Vlasselaer |
| 5,585,007 A | 12/1996 | Antanavich et al. |
| 5,589,462 A | 12/1996 | Patat et al. |
| 5,601,727 A | 2/1997 | Bormann et al. |
| 5,607,579 A | 3/1997 | Latham, Jr. et al. |
| 5,614,106 A | 3/1997 | Payrat et al. |
| 5,632,905 A | 5/1997 | Haynes |
| 5,641,622 A | 6/1997 | Lake et al. |
| 5,643,192 A | 7/1997 | Hirsh et al. |
| 5,643,193 A | 7/1997 | Papillon et al. |
| 5,674,173 A | 10/1997 | Hlavinka et al. |
| 5,733,545 A | 3/1998 | Hood, III |
| 5,736,033 A | 4/1998 | Coleman et al. |
| 5,762,798 A | 6/1998 | Wenthold et al. |
| 5,788,662 A | 8/1998 | Antanavich et al. |
| 5,795,489 A | 8/1998 | Holm et al. |
| 5,795,571 A | 8/1998 | Cederholm-Williams et al. |
| 5,853,600 A | 12/1998 | McNeal et al. |
| 5,860,937 A | 1/1999 | Cohen |
| 5,889,584 A | 3/1999 | Wardlaw |
| 5,918,622 A | 7/1999 | Perez et al. |
| 5,924,972 A | 7/1999 | Turvaville et al. |
| 5,934,803 A | 8/1999 | Hutter |
| 5,980,757 A | 11/1999 | Brown et al. |
| 6,011,490 A | 1/2000 | Tonnesen et al. |
| 6,022,306 A | 2/2000 | Dumont et al. |
| 6,025,201 A | 2/2000 | Zelmanovic et al. |
| 6,027,655 A | 2/2000 | Holm |
| 6,051,146 A | 4/2000 | Green et al. |
| 6,053,856 A | 4/2000 | Hlavinka |
| 6,054,122 A | 4/2000 | MacPhee et al. |
| 6,063,297 A | 5/2000 | Antanavich et al. |
| 6,071,423 A | 6/2000 | Brown et al. |
| 6,090,793 A | 7/2000 | Zimmermann et al. |
| 6,096,309 A | 8/2000 | Prior et al. |
| 6,102,843 A | 8/2000 | Kelley et al. |
| 6,117,425 A | 9/2000 | MacPhee et al. |
| 6,153,113 A | 11/2000 | Goodrich et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,214,338 B1 | 4/2001 | Antanavich et al. |
| 6,245,900 B1 | 6/2001 | Yamasaki et al. |
| 6,277,961 B1 | 8/2001 | Hock et al. |
| 6,280,400 B1 | 8/2001 | Niermann |
| 6,296,602 B1 | 10/2001 | Headley |
| 6,316,247 B1 | 11/2001 | Katz et al. |
| 6,322,785 B1 | 11/2001 | Landesberg et al. |
| 6,334,842 B1 | 1/2002 | Hlavinka et al. |
| 6,342,157 B1 | 1/2002 | Hood, III |
| 6,368,298 B1 | 4/2002 | Beretta et al. |
| 6,464,624 B2 | 10/2002 | Pages |
| 6,472,162 B1 | 10/2002 | Coelho et al. |
| 6,516,953 B1 | 2/2003 | DiCesare et al. |
| 6,544,162 B1 | 4/2003 | Van Wie et al. |
| 6,563,953 B2 | 5/2003 | Lin et al. |
| 6,629,919 B2 | 10/2003 | Egozy et al. |
| 6,676,629 B2 | 1/2004 | Andrew et al. |
| 6,758,978 B1 | 7/2004 | Bedell |
| 6,764,531 B2 | 7/2004 | Hogan |
| 6,777,231 B1 | 8/2004 | Katz et al. |
| 6,905,612 B2 | 6/2005 | Dorian et al. |
| 6,979,307 B2 | 12/2005 | Beretta et al. |
| 7,011,644 B1 | 3/2006 | Andrew et al. |
| 7,077,273 B2 | 7/2006 | Ellsworth et al. |
| 7,179,391 B2 | 2/2007 | Leach et al. |
| 2002/0032112 A1 | 3/2002 | Pages |
| 2002/0076400 A1 | 6/2002 | Katz et al. |
| 2003/0082152 A1 | 5/2003 | Hedrick et al. |
| 2003/0191429 A1 | 10/2003 | Andrew et al. |
| 2004/0171146 A1 | 9/2004 | Katz et al. |
| 2004/0182788 A1 | 9/2004 | Dorian et al. |
| 2004/0182795 A1 | 9/2004 | Dorian et al. |
| 2004/0251217 A1 | 12/2004 | Leach et al. |
| 2005/0076396 A1 | 4/2005 | Katz et al. |
| 2005/0084961 A1 | 4/2005 | Hedrick et al. |
| 2005/0109716 A1 | 5/2005 | Leach et al. |
| 2005/0153441 A1 | 7/2005 | Hedrick et al. |
| 2005/0153442 A1 | 7/2005 | Katz et al. |
| 2005/0196874 A1 | 9/2005 | Dorian et al. |
| 2005/0247715 A1 | 11/2005 | Ellsworth et al. |
| 2005/0260174 A1 | 11/2005 | Fraser et al. |
| 2005/0260175 A1 | 11/2005 | Hedrick et al. |
| 2005/0282275 A1 | 12/2005 | Katz et al. |
| 2006/0083720 A1 | 4/2006 | Fraser et al. |
| 2006/0175242 A1 | 8/2006 | Dorian et al. |
| 2006/0175244 A1 | 8/2006 | Dorian et al. |
| 2006/0196885 A1 | 9/2006 | Leach et al. |
| 2006/0243676 A1 | 11/2006 | Swift et al. |
| 2007/0036768 A1 | 2/2007 | Fraser et al. |
| 2007/0075016 A1 | 4/2007 | Leach |
| 2008/0011684 A1 | 1/2008 | Dorian et al. |
| 2008/0283474 A1 | 11/2008 | Leach et al. |
| 2009/0289014 A1 | 11/2009 | Hoeppner |
| 2010/0206798 A1 | 8/2010 | Dorian et al. |
| 2010/0226909 A1 | 9/2010 | Hecker et al. |

FOREIGN PATENT DOCUMENTS

| | | |
|---|---|---|
| BR | 9103724 | 3/1993 |
| CA | 1321138 | 8/1993 |
| CA | 2182862 | 6/1996 |
| CN | 1074709 | 7/1993 |
| DE | 56103 | 10/1860 |
| DE | 1443359 | 11/1968 |
| DE | 4202667 | 5/1993 |
| EP | 090997 | 10/1983 |
| EP | 0102773 | 3/1984 |
| EP | 0109374 | 5/1984 |
| EP | 0142339 | 5/1985 |
| EP | 0253198 | 1/1988 |
| EP | 0272915 A2 | 6/1988 |
| EP | 285891 | 10/1988 |
| EP | 0295771 | 12/1988 |
| EP | 0417818 | 3/1991 |
| EP | 0534178 | 3/1993 |
| EP | 0592242 | 4/1994 |
| EP | 1005910 | 6/2000 |
| EP | 1427279 A1 | 6/2004 |
| EP | 1467746 A2 | 10/2004 |
| EP | 1670315 A2 | 6/2006 |
| EP | 1716901 | 11/2006 |
| GB | 854715 | 11/1960 |
| JP | 60-053845 | 3/1985 |
| JP | 60250014 A | 12/1985 |
| JP | 63182055 A | 7/1988 |
| JP | 6454256 | 4/1989 |
| JP | 2036872 | 2/1990 |
| JP | 02071747 | 3/1990 |
| JP | 04500170 T | 1/1992 |
| JP | 6250014 A | 9/1994 |
| JP | 09187504 A | 7/1997 |
| JP | 9509432 T | 9/1997 |
| JP | 11502502 T | 3/1999 |
| JP | 2000117150 A | 4/2000 |
| JP | 02129224 | 10/2000 |
| JP | 2001017540 A | 1/2001 |
| JP | 2005523128 T | 8/2005 |
| MX | 246078 | 5/2007 |
| WO | WO-8400905 | 3/1984 |

| | | |
|---|---|---|
| WO | WO-8802259 | 4/1988 |
| WO | WO-8901827 A1 | 3/1989 |
| WO | WO-9010031 | 9/1990 |
| WO | WO-9222312 | 12/1992 |
| WO | WO-9305067 | 3/1993 |
| WO | WO-9308904 | 5/1993 |
| WO | WO-9407548 | 4/1994 |
| WO | WO-9616714 A1 | 6/1996 |
| WO | WO-9617871 A1 | 6/1996 |
| WO | WO-9848938 | 11/1998 |
| WO | WO-0103756 | 1/2001 |
| WO | WO-0183068 | 11/2001 |
| WO | WO-0224107 | 3/2002 |
| WO | WO-03015800 | 2/2003 |
| WO | WO-03024215 A1 | 3/2003 |
| WO | WO-03053362 A2 | 7/2003 |
| WO | WO-03090839 A1 | 11/2003 |
| WO | WO-03092894 | 11/2003 |
| WO | WO-2004009207 | 1/2004 |
| WO | WO-2004037427 A1 | 5/2004 |
| WO | WO-2004104553 | 12/2004 |
| WO | WO-2005034843 A2 | 4/2005 |
| WO | WO-2006081699 A1 | 8/2006 |
| WO | WO-2007142908 A1 | 12/2007 |

OTHER PUBLICATIONS

"Cell Isolation Theory, Tissue Types," (2004) (5 pages) Worthington Biochemical Corp.

"Cytori Celution Cell Concentrate Device," Exhibit 14, 510(k) Summary, FDA approval K060482 (Sep. 28, 2006).

"Frequently Asked Questions, 1. Kits, 2. Engzymes," (2003) 3 pages Worthington Biochemical Corp.

"Sefar Solutions for the Healthcare Industry," brochure (2003) 9 pages Sefar Medifab®.

"Trypsinization of Adherent Cells," (undated) 2 pages.

Anesthesiology, vol. 81, No. 4, pp. 1074-1077, Oct. 1994, Hiromasa Mitsuhata, M.D., et al., "An Anaphylactic Reaction to Topical Fibrin Glue".

Ann Thorac Surg, vol. 53, pp. 530-531, 1992, Mehmet C. Oz, M.D., et al., "Autologous Fibrin Glue From Intraoperatively Collected Platelet-Rich Plasma".

Ann Thorac Surg, vol. 56, pp. 387-389, 1993, Robert L. Quigley, M.D., et al., "Intraoperative Procurement of Autologous Fibrin Glue".

Berguer; R., R. L. Staerkel, E. E. Moore, F. A. Moore, W. B. Galloway, and M. B. Mockus. "Warning: fatal reaction to the use of fibrin glue in deep hepatic wounds. Case reports." *J Trauma* 31 (Mar. 1991): 408-11.

Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular operations. Development of thrombin and factor V inhibitors," *J Thorac Cardiovasc Surg* 105 (May 1993): 892-7.

Biopolymers, vol. 27, pp. 763-774, 1988, Gerald Marx, "Mechanism of Fibrin Coagulation Based on Selective, Cation-Driven, Protofibral Association".

Casali, B., F. Rodeghiero, A. Tosetto, B. Palmieri, R. Immovilli, C. Ghedini, and P. Rivasi. "Fibrin glue from single-donation autologous plasmapheresis." Transfusion 32 (Jul. 1992): 641-3.

Collier, B.S. et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda, Md. 20014, Blood, vol. 47, No. 5 May 1976.

DelRossi, A. J., A. C. Cernaianu, R. A.Vertrees, C. J. Wacker, S. J. Fuller, J. Cilley Jr., and W. A. Baldino. "Platelet-rich plasma reduces postoperative blood loss after cardiopulmonary bypass." *J Thorac Cardiovasc Surg* 100 (Feb. 1990): 281-6.

DeUgarte, M.D., Daniel A., et al., "Future of Fat as Raw Material for Tissue Regneration," (2007) pp. 215-219, Lippincott Williams & Wilkins, Inc.

DiMuzio, Paul et al., "Development of a Tissue-Engineered Bypass Graft Seeded with Stem Cells," Vasucular, vol. 14, No. 6, (2006) pp. 338-342, BC Decker, Inc.

Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".

Edlich, Richard F., George T. Rodeheaver, and John G. Thacker. "Surgical Devices in Wound Healing Management." In *Wound Healing: Biochemical & Clinical Aspects*,ed. I. Kelman Cohen, Robert F. Diegelmann, and William J. Lindblad. 581-600. 1st ed., vol. Philadelphia: W.B. Saunders Company, 1992).

Epstein, G. H., R. A. Weisman, S. Zwillenberg, and A. D. Schreiber. "A new autologous fibrinogen-based adhesive for otologic surgery." *Ann Otol Rhinol Laryngol* 95 (1 Pt 1 1986): 40-5.

First clinical results: Kuderma, H. and Helene Matras. "Die klinische Anwendung der Klebung van Nervenanastomosen mit Gerinnungssubstanzen bei der Rekonstruction verletzter peripherer Nerven." Wein Klin Wochenschr 87 (15 1975): 495-501.

Frasier, John K., et al., "Plasticity of human adipose stem cells toward endothelial cells and cardiomyocytes," Nature Clinical Practice Cardiovascular Medicine, vol. 3, Supplement 1 (Mar. 2006) pp. S33-S37.

Gibble, J. W. and P. M. Ness. "Fibrin glue: the perfect operative sealant?" *Transfusion* 30 (Aug. 1990): 741-7.

Gimble, Jeffrey M., "Adipose-Derived Stem Cells for Regenerative Medicine," Circulation Research (2007) pp. 1249-1260, American Heart Association, Inc.

Gomillion, Cheryl T., et al., "Stem cells and adipose tissue engineering," Biomaterials 27, Science Direct (2006) pp. 6052-6063, Elsevier.

GPS® III System, GPS® III Platelet Separation System, Leadership through Technology, brochure, Jul. 2007 (8 sheets).

GPS® System, "GPS® Platelet Concentrate System," Cell Factor Technologies, Inc., Biomet Orthopaedics, Inc., (2004) (9 pages).

GPS® System, "Shoulder Recovery with the GPS® Platelet Concentrate System, Rotator Cuff Surgical Techniques," brochure, Cell Factor Technologies, Inc., Biomet Orthopaedics, Inc., (2004) 6 pages.

GPS® System, "Shoulder Recovery with the GPS® Platelet Concentrate System, Rotator Cuff Surgical Techniques," Cell Factor Technologies, Inc., Biomet Orthopaedics, Inc., (2004) 3 pages, http://www.cellfactortech.com/global_products.cfm, printed Sep. 16, 2005.

GPS®II System, Gravitational Platelet Separation System, "Accelerating the Body's Natural Healing Process," Cell Factor Technologies, Inc., Biomet Europe (2005) 16 pages, http://www.cellfactortech.com/global_products.cfm, printed Sep. 16, 2005.

GPS®II System, Gravitational Platelet Separation System, "User Manual," Cell Factor Technologies, Inc., Biomet Europe [date unknown] 13 pages, http://www.cellfactortech.com/global_products.cfm, printed Sep. 16, 2005.

Guilak, Frank, et al., "Adipose-derived adult stem cells for cartilage tissue engineering," Biorheology 41 (2004) pp. 389-399, IOS Press.

Harris, E.L.V. Concentration of the Extract. In. Protein Purification Methods: A Practical Approach Harris, E.L.V.; Angal, S.; Editors. (1989) Publisher: (IRL Press, Oxford, UK), pp. 67-69.

Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (3 1992):357-9.

Hattori, et al., "Osteogenic Potential of Human Adipose Tissue-Derived Stromal Cells as an Alternative Stem Cell Source," Cells Tissues Organs (2004) 178:2-12 Karger.

Hennis, H. L., W. C. Stewart, and E. K. Jeter. "Infectious disease risks of fibrin glue [letter]." *Ophthalmic Surg* 23 (9 1992): 640.

International Preliminary Examination Report and Written Opinion issued Aug. 31, 2010 for PCT/US2009/035564 claiming benefit of U.S. Appl. No. 61/078,178, filed Jul. 3, 2008 of which U.S. Appl. No. 12/395,085, filed Feb. 27, 2009 claims benefit.

International Preliminary Report on Patentability mailed Feb. 12, 2009, for PCT/US2007/017055 filed Jul. 31, 2007, which claims benefit of U.S. Appl. No. 60/834,550, filed Jul. 31, 2006, based on U.S. Appl. No. 60/723,312, filed Oct. 4, 2005; U.S. Appl. No. 60/654,718, filed Feb. 17, 2005; and U.S. Appl. No. 60/651,050, filed Feb. 7, 2005.

International Search Report and Written Opinion for PCT/US2006/003597 mailed Feb. 6, 2006.
International Search Report and Written Opinion for PCT/US2006/003599 mailed Aug. 21, 2006.
International Search Report and Written Opinion mailed Aug. 12, 2008 for PCT/US07/17055.
International Search Report and Written Opinion mailed Jul. 3, 2009 for PCT/US2009/035564 claiming benefit of U.S. Appl. No. 61/078,178, filed Jul. 3, 2008.
Jackson, C. M. and Y. Nemerson. "Blood coagulation." *Annu Rev Biochem* 49 (811 1980):765-811).
Journal of Biomaterials Applications, vol. 7, pp. 309-353, Apr. 1993, David H. Sierra, "Fibrin Sealant Adhesive Systems: A review of their Chemistry, Material Properties and Clinical Appllications".
Journal of Oral Maxillofacial Surgery, vol. 43, pp. 605-611, 1985, Helene Matras, M.D., "Fibrin Seal: The State of the Art".
Kjaergard, H. K U. S. Weis-Fogh, H. Sorensen, J. Thiis, and I. Rygg. "A simple method of preparation of autologous fibrin glue by means of ethanol." *Surg Gynecol Obstet* 175 (Jan. 1992):72-3.
Kjaergard, H. K., Fogh Us Weis, and J. J. Thiis. "Preparation of autologous fibrin glue from pericardial blood." *Ann Thorac* Sur 55 (Feb. 1993): 543-4.
Laryngoscope vol. 99, pp. 974-976, Sep. 1989, Kyosti Laitakari, M.D., et al., "Autologous and Homologous Fibrinogen Sealants: Adhesive Strength".
Laryngoscope, vol. 95, pp. 1074-1076, Sep. 1985, Karl H. Siedentop, M.D., et al., "Autologous Fibrin Tissue Adhesive".
Laryngoscope, vol. 96, pp. 1062-1064, Oct. 1986, Karl H. Siedentop, M.D., et al., "Extended Experimental and Preliminary Surgical Findings with Autologous Fibrin Tissue Adhesive Made from Patient's Own Blood".
Lendeckel, Stefan, et al., "Autologous stem cells (adipose) and fibrin glue used to treat widespread traumatic calvarial defects: case report," Journal of Cranio-Maxillofacial Surgery (2004) European Association for Cranio-Maxillofacial Surgery.
Lerner, R. and N. S. Binur. "Current status of surgical adhesives." *J Surg Res* 48 (Feb. 1990):165-81.
Marrowstim™ Concentration System, (2008) 20 pages Biomet Biologics, Inc.
Matras, Helene, H. P. Dinges, H. Lassmann, and B. Mamoli. "Zur nahtlosen interfaszikularen Nerventransplantation im Tierexperiment." Wein Med Woschtr 122 (37 1972): 517-523.
Moretz, W., Jr., J Shea Jr., J. R. Emmett, and J Shea. "A simple autologous fibrinogen glue for otologic surgery." *Otolaryngol Head Neck Surg* 95 (Jan. 1986): 122-4.
Nakagami, Hironori, et al., "Novel Autologous Cell Tehrapy in Ischemic Limb Disease Through Growth Factor Secretion by Cultured Adipose Tissue-Derived Stromal Cells," Angiogenesis by Adipose Tissue-Derived Cells, (2005) pp. 2542-2547, American Heart Association, Inc.
Nathan, Suresh et al., "Cell-Based Therapy in the Repair of Osteochondral Defects: A Novel Use for Adipose Tissue," Tissue Engineering, vol. 9, No. 4 (2003) pp. 733-744 Mary Ann Liebert, Inc.
Office Action mailed Apr. 6, 2010 for Japanese Application No. 2007-554193 filed Aug. 23, 2007 has been provided including a partial translation thereof, which cites JP11-502502 and JP2001017540. Japanese Application No. 2007-554193 claims benefit of PCT/US2006/003599, filed Jan. 30, 2006; claiming priority from U.S. Appl. Nos. 60/651,050, filed Feb. 7, 2005; 60/654,718, filed Feb. 17, 2005; and 60/723,312, filed Oct. 4, 2005 of which U.S. Appl. No. 11/831,605, filed Jul. 31, 2007 and U.S. Appl. No. 12/772,497, filed May 3, 2010 claim benefit.
Office Action mailed Apr. 6, 2010 for Japanese Application No. 2007554191 filed Aug. 7, 2007 has been provided including a partial translation thereof, which also cites JP2001017540. Japanese Application No. 2007554191 claims benefit of PCT/US2006/003597, filed Jan. 30, 2006; claiming priority from U.S. Appl. Nos. 60/651,050, filed Feb. 7, 2005; 60/654,718, filed Feb. 17, 2005; and 60/723,312, filed Oct. 4, 2005 of which U.S. Appl. No. 11/831,605, filed Jul. 31, 2007 and U.S. Appl. No. 12/772,497, filed May 3, 2010 claim benefit.
Office Action mailed Sep. 14, 2010 for Japanese Application No. 2007-554193 filed Aug. 23, 2007 has been provided including a partial translation thereof. Japanese Application No. 2007-554193 claims benefit of PCT/US2006/003599, filed Jan. 30, 2006; claiming priority from U.S. Appl. Nos. 60/651,050, filed Feb. 7, 2005; 60/654,718, filed Feb. 17, 2005; and 60/723,312, filed Oct. 4, 2005 of which U.S. Appl. No. 11/831,605, filed Jul. 31, 2007 and U.S. Appl. No. 12/772,497, filed May 3, 2010 claim benefit.
Office Action mailed Sep. 14, 2010 for Japanese Application No. 2007554191 filed Aug. 7, 2007 has been provided including a partial translation thereof. Japanese Application No. 2007554191 claims benefit of PCT/US2006/003597, filed Jan. 30, 2006; claiming priority from U.S. Appl. Nos. 60/651,050, filed Feb. 7, 2005; 60/654,718, filed Feb. 17, 2005; and 60/723,312, filed Oct. 4, 2005 of which U.S. Appl. No. 11/831,605, filed Jul. 31, 2007 and U.S. Appl. No. 12/772,497, filed May 3, 2010 claim benefit.
Otolaryngologic Clinics of North America, vol. 27, No. 1, pp. 203-209, Feb. 1994, Dean M. Toriumi, M.D., et al., "Surgical Tissue Adhesives in Otolaryngology-Head and Neck Surgery".
Parker, Anna M., et al., Adipose-derived stem cells for the regeneration of damaged tissues, Expert Opinion, Cell- & Tissue-based Therapy, Expert Opin. Biol. Ther. (2006) pp. 567-578 Informa UK Ltd.
Planat-Bénard, V., et al., "Spontaneous Cardiomyocyte Differentiation From Adipose Tissue Stroma Cells," Adipose-Derived Cell Cardiomyocyte (2004) pp. 223-229 American Heart Association, Inc.
Plasmax™ Plasma Concentrate, brochure (2006) 5 pages Biomet Biologics, Inc.
Rangappa, Sunil, M.D., "Transformation of Adult Mesenchymal Stem Cells Isolated From the Fatty Tissue Into Cardiomyocytes," Adult Stem Cells Transformed into Cardiomyoctyes, (2003) pp. 775-779 Ann Thorac Surg.
Rigotti, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Breast, PRS Journal vol. 119, No. 5, Stem Cell Therapy for Angiogenesis, (Pub. 2005) pp. 1409-1422.
Rubin, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Discussion vol. 119, No. 5, Stem Cell Therapy for Angiogenesis, (2007) pp. 1423-1424.
Sanal, M. "Does fibrin glue cause foreign body reactions? [letter]." *Eur J Pediatr Surg* 3 (3 1993): 190 (1 page).
Sanal, M., H. Dogruyol, A. Gurpinar, and O. Yerci. "Does fibrin glue cause foreign body reactions?" *Eu r J Pediatr Surg* 2 (May 1992): 285-6.
Schäffler, Andreas, et al., "Concise Review: Adipose Tissue-Derived Stromal Cells—Basic and Clinical Implications for Novel Cell-Based Therapies," Tissue-Specific Stem Cells, Stem Cells® (2007) pp. 818-827 AlphaMed Press.
Sigma-Aldrich® Alkaline Phosphatase (Procedure No. 85), drug fact sheet, (2003) pp. 1-2, Sigma-Aldrich, Inc.
Takahashi, Kazutoshi et al., "Induction of Pluripotent Stem Cells from Adult Human Fibroblasts by Defined Factors," Cell, (2007) pp. 1-12, Elsevier Inc.
The American Journal of Surgery, vol. 168, pp. 120-122, Aug. 1994, Roy L. Tawes, Jr., M.D., et al., "Autologous Fibrin Glue: The Last Step in Operative Hemostatis".
The American Surgeon, vol. 55, pp. 166-168, Mar. 1989, William D. Spotnitz, M.D., et al., "Successful Use of Fibrin Glue During 2 Years of Surgery at a University Medical Center".
Vortech™ Concentration System, "Do you want a sticky gel to improve the handling of your bone graft?, Platelet Rich Plasma Concentrate, High Volume in 5 Minutes," Biomet Biologics, Inc., Aug. 2005.
Vox Sanquinis, vol. 68: 82-89, Feb. 1995, Boomgaard Et. al, Pooled Platelet Concentration Prepred by the . . . .
Weis-Fogh, U. S. "Fibrinogen prepared from small blood samples for autologous use in a tissue adhesive system." *Eur Surg* Res 20 (5-6 1988): 381-9.
Wiseman, David M., David T. Rovee, and Oscar M. Alverez. "Wound Dressings: Design and Use." in *Wound Healing: Biochemical & Clinical Aspects*,ed. I. Kelman Cohen, Robert F. Diegelmann, and William J. Lindblad. 562-580. 1st ed., vol. Philadelphia: W. B. Saunders Company, 1992).

Yoon, Eulsik, M.D., Ph.D., et al., "In Vivo Osteogenic Potential of Human Adipose-Derived Stem Cells/Poly Lactide-Co-Glycolic Acid Constructs for Bone Regneration in a Rat Critical-Sized Calvarial Defect Model," Tissue Engineering, vol. 13, No. 3 (2007) pp. 619-627 Mary Ann Liebert, Inc.

Zhang, Duan-zhen, et al., "Transplantation of autologous adipose-derived stem cells ameliorates cardiac function in rabbits with myocardial infarction," Chinese Medical Journal, vol. 120, No. 4 (2007) pp. 300-307 General Hospital of Shenyang Military Region, Shenyang, China.

Zuk, Patricia A., Ph.D., "Multilineage Cells from Human Adipose Tissue: Implications for Cell-Based Therapies," Tissue Engineering, vol. 7, No. 2, (2001) pp. 211-228 Mary Ann Liebert, Inc.

"Trypsinizing cells." Bart's Cookbook, Web. Apr. 14, 2010. http://pingu.salk.edu/~sefton/Hyper_protocols/trypsin.html.

DePalma, L., et al., "The preparation of fibrinogen concentrate for use as fibrin glue by four different methods." Transfusion (1993) vol. 33, No. 9; pp. 717-720.

Friesen, M.D., Robert, et al. "Blood Conservation During Pediatric Cardiac Surgery: Ultrafiltration of the Extracorporeal Circuit Volume After Cardiopulmonary Bypass." Anesth. Analg 1993: 77-702-7.

Hood, Andrew G., et al., "Perioperative Autologous Sequestration III: A New Physiologic Glue with Wound Healing Properties," (Jan. 1993) vol. 14 pp. 126-129.

Longas, Maria O., "An Improved Method for the Purification of Human Fibrinogen." J. Biochem (1980) vol. 11, pp. 559-564.

Marx, Gerard, et al., "Heat Denaturation of Fibrinogen to Develop a Biomedical Matrix." Journal of Biomedical Materials Research Part B: Applied Biomaterials (Apr. 2007) pp. 49-57.

Masri, Marwan A., et al. "Isolation of Human Fibrinogen of High Purity and in High Yield Using Polyethylene Glycol 1000." Thromb Haemostas (Struttgart) (1983) vol. 49 (2); pp. 116-119.

Orphardt, Charles E., "Denaturation of Proteins," Virtual Chembook, Elmhurst College (2003) 3 pages. http://www.elmhurst.edu/~chm/vchembook/568denaturation.html (web accessed Mar. 9, 2011).

Silver, Frederick H., et al., "Review Preparation and use of fibrin glue in surgery." Biomaterials 16 (1995) pp. 891-903.

Solem, Jan Otto, et al., "Hemoconcentration by Ultrafiltration During Open-Heart Surgery," Scand J Thor Cardiovasc Surg 22:271-274, 1988.

Sutton, Robin G., et al. "Comparison of Three Blood-Processing Techniques During and After Cardiopulmonary Bypass." Ann Thorac Surg (1993) vol. 56; pp. 941-943.

Weisman, MD., Robert A., "Biochemical Characterization of Autologous Fibrinogen Adhesive," Laryngoscope 97: Oct. 1987; pp. 1186-1190.

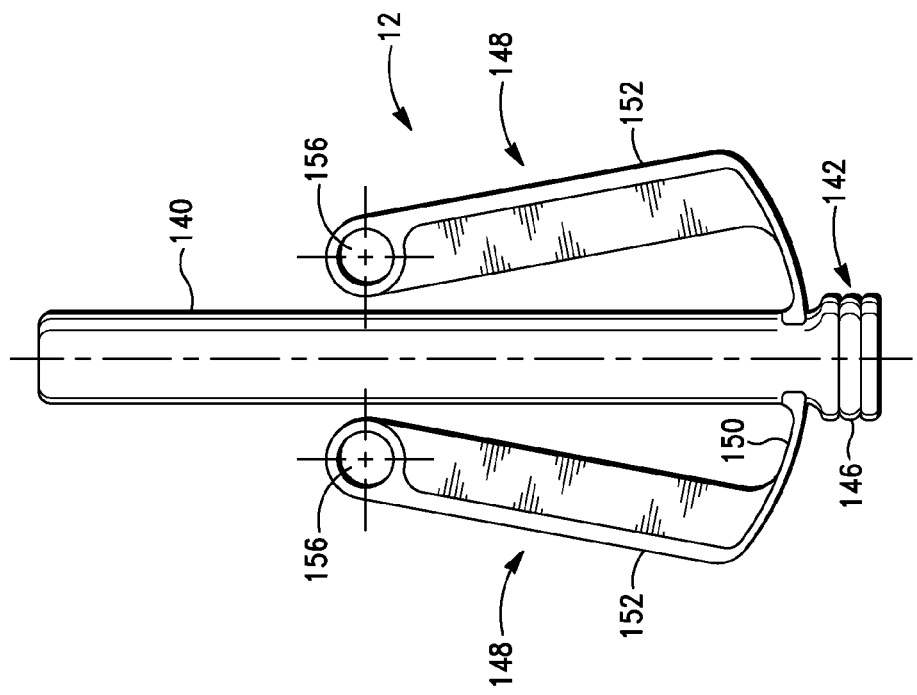
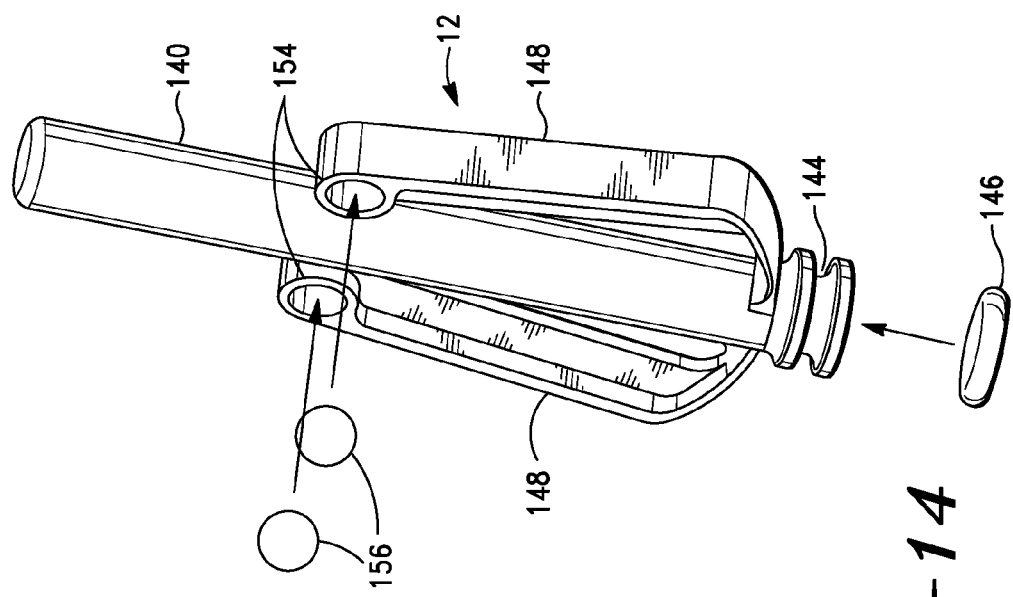

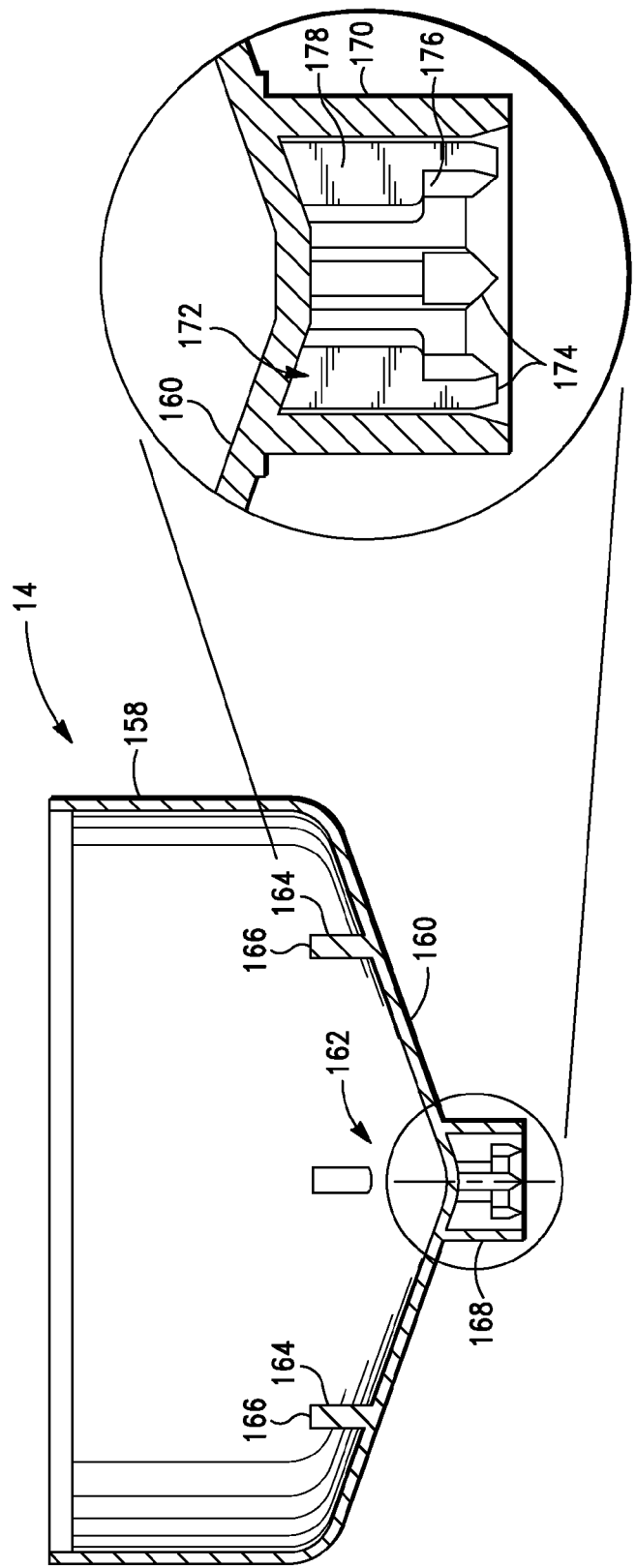

FIG.—35

METHOD FOR PREPARING PLATELET RICH PLASMA AND CONCENTRATES THEREOF

CROSS-REFERENCE TO RELATED APPLICATIONS

This application is a divisional of U.S. patent application Ser. No. 11/831,605 filed Jul. 31, 2007, now U.S. Pat. No. 7,866,485, issued on Jan. 11, 2011, which is (a.) a continuation-in-part of U.S. patent application Ser. No. 11/342,749 filed Jan. 30, 2006, now U.S. Pat. No. 7,824,559 issued on Nov. 2, 2010, which claims the benefit of (1.) U.S. Provisional Application No. 60/723,312, filed on Oct. 4, 2005; (2.) U.S. Provisional Application No. 60/654,718, filed on Feb. 17, 2005; and (3.) U.S. Provisional Application No. 60/651,050, filed on Feb. 7, 2005; and (b.) also claims the benefit of the U.S. Provisional Application No. 60/834,550, filed on Jul. 31, 2006. The disclosures of the above applications are incorporated herein by reference.

FIELD

This disclosure relates to a device and method for preparing platelet-plasma concentrates with wound healing properties for use as a tissue sealant, adhesive, etc. The concentrates have a fully active (un-denatured) fibrinogen concentration that is greater than the concentration of fibrinogen in whole blood and a platelet concentration that is greater than the concentration of platelets in whole blood.

BACKGROUND

Blood can be fractionated, and the different fractions of the blood are useful for different medical needs. Under the influence of gravity or centrifugal force, blood can separate into three layers. At equilibrium, the top low-density layer is a straw-colored clear fluid called plasma. Plasma is a water solution of salts, metabolites, peptides, and many proteins ranging from small (insulin) to larger molecules (complement components).

The bottom, high-density layer is a deep red viscous fluid comprising unnucleated red blood cells (erythrocytes) specialized for oxygen transport. The red color is imparted by a high concentration of chelated iron or heme that is responsible for the erythrocytes' high specific gravity. The relative volume of whole blood that consists of erythrocytes is called the hematocrit, and in normal human beings this can range from about 30% to about 60%, such as about 37% to about 52% of whole blood.

The intermediate layer can be the smallest, appearing as a thin white band above the erythrocyte layer and below the plasma layer; this is called the buffy coat. The buffy coat itself has two major components, nucleated leukocytes (white blood cells) and a nuclear smaller bodies called platelets (or thrombocytes). Leukocytes confer immunity and contribute to debris scavenging. Platelets seal ruptures in blood vessels to stop bleeding, and deliver growth and wound healing factors to a wound site. Slower speed centrifugation or shorter duration centrifugation permits separation of erythrocytes and leukocytes from plasma, while the smaller platelets remain suspended in the plasma, resulting in platelet rich plasma (PRP).

U.S. Pat. No. 5,585,007 identifies methods for making plasma concentrates from whole blood for use in wound healing and as a tissue sealant. This patent is hereby incorporated by reference in its entirety. This device, designed for placement in a medical laboratory or surgical amphitheatre, uses a disposable cartridge for preparing tissue sealant. The device was particularly applicable for stat preparations of autologous tissue sealants. Preparation in the operating room of about 5 ml of sealant from about 50 ml of patient blood required less than about 15 minutes. There was reduced risk of tracking error because preparation could take place in the operating room during the surgical procedure. Chemicals added could be limited to anticoagulant (e.g., citrate) and calcium chloride. The disposable cartridge could fit in the palm of the hand and was hermetically sealed to reduce exposure to patient blood and to ensure sterility. Adhesive and tensile strengths of the product were comparable or superior to pooled blood fibrin sealants made by precipitation methods. Use of antifibrinolytic agents (such as aprotinin) was not necessary because the tissue sealant contained high concentrations of natural inhibitors of fibrinolysis from the patient's blood.

This device used a new sterile disposable cartridge with the separation chambers for each run. Since the device was designed to be used in a normal medical setting with ample power, the permanent components were designed for long-term durability, safety and reliability, and were relatively heavy, using conventional centrifuge motors and accessories.

Small, self-contained centrifugal devices for obtaining platelet concentrates from blood are described in, copending U.S. patent application Ser. No. 10/394,828 filed Mar. 21, 2003, the entire contents of which are hereby incorporated by reference. This device separates blood into erythrocyte, plasma, and platelet layers. The device can be used to selectively remove the platelet layer as a platelet concentrate, that is, platelets suspended in a minimal amount of plasma.

Platelet rich plasma is a concentrated platelet product that can be produced from whole blood through commercially available systems, resulting in varying levels of platelet concentration. Platelets play a crucial role in the signaling cascade of normal wound healing. Activated platelets release the contents of their α-granules resulting in a deposition of powerful growth factors such as platelet derived growth factor (PDGF), transforming growth factor 'β-(TGF-β)', vascular endothelial growth factor (VEGF), and epidermal growth factor (EGF). PRP has been used in many different clinical applications, demonstrating the effectiveness and importance of the product for a variety of medical procedures. For example, percutaneous application of PRP to patients with severe lateral epicondylitis, 'i.e. tennis elbow' resulted in improved elbow function and reduced pain. Early maturation of bony fusion was observed when platelet concentrate was used during lumbar spinal fusions. Chronic diabetic foot ulcers treated with PRP achieved increased healing rates compared to the control group receiving standard care. Studies by S. Bhanot, and J. C Alex, *FACIAL PLASTIC SURGERY*, 18(1): 27-33 (2002) show decreased formation of hematoma and seroma, decreased postoperative swelling, and improved healing time for plastic surgeries that included PRP in the treatment. Further, during dental surgeries, the use of PRP has improved bone regeneration around implants.

PRP have demonstrated numerous clinical benefits to patients. Concentrations of at least about $1,000 \times 10^3$ platelets/μL may be useful. The system described in copending U.S. patent application Ser. No. 10/394,828 can provide platelets up to about 8 times baseline concentration, and the normal human platelet range is about $200 \times 10^3$ platelets/μL to about $400 \times 10^3$ platelets/μL. This means a highly effective concentrate in a range of about $1,600 \times 10^3$ platelets/μL to about $3,200 \times 10^3$ platelets/μL.

SUMMARY

A PRP (Platelet Rich Plasma) separator assembly can comprise a cylindrical outer wall closed at the top by an upper plate and closed at the bottom. The outer wall has an inner surface. A cylindrical inner wall concentric with a cylindrical outer wall can having a top edge and a bottom. The inner wall defines a central axis. The bottom of the inner wall is closed by a sloped bottom plate having a central opening, the bottom plate has an upper surface sloped down to a central opening. The top edge of the inner wall terminates at a distance from the upper plate to define an annular erythrocyte passageway therebetween. The inner wall has an outer surface and an inner surface that slopes radially inward from a top edge to a bottom at an angle of from about 0.2 to about 5 degrees relative to a central axis of the inner wall. A cylindrical depth filter is positioned between the inner surface of the outer wall and the outer surface of the inner wall in communication with the inner wall through the erythrocyte passageway.

The distance between the top of the inner wall and the upper plate can be from about 0.02 to about 50 mm, such as about 0.02 mm to about 10 mm. The depth filter can extend beyond the top edge of the inner wall. According to various, embodiments, the upper plate has a bottom surface, and the depth filter extends to the bottom surface.

For producing platelet rich plasma concentrate for wound healing, the depth filter can have the capacity to accept up to or more than about 85 percent of the hematocrit value of a patient's blood and less than a major portion of the platelet rich plasma remaining after the erythrocytes separation from a patient's blood.

For producing platelet rich plasma concentrate for hemostasis, the depth filter can have the capacity to accept up to or more than about 97 percent of the hematocrit value of a patient's blood and less than a major portion of the platelet rich plasma remaining after the erythrocytes separation from a patient's blood.

For all applications, the depth filter can have the capacity to accept up to or more than about 99 percent of the hematocrit value of a patient's blood and less than a major portion of the platelet rich plasma remaining after the erythrocytes separation from a patient's blood.

The depth filter can have the capacity to accept about 100 percent of the hematocrit value of a patient's blood and less than a major portion of the platelet rich plasma remaining after the erythrocytes separation from a patient's blood.

The PRP separator can be mounted for rotation about an outlet tube concentric with the central axis.

The separation chamber can include a balanced array of separator plates extending radially inward from the inner wall and upward from the bottom plate, the separation chamber can be balanced for substantially vibration-free rotation about the central axis.

The PRP separator-concentrator assembly can comprise the PRP separation assembly described above in combination with a PRP concentrator assembly. The concentration assembly has a PRP concentration sump; an axially concentric rigid stationary outlet tube secured to the housing and extending through the PRP separation assembly to the PRP concentrate sump; and the PRP separation assembly is attached to and positioned above the PRP concentration assembly to form a combined separator-concentrator assemblage that is rotatable about the outlet tube.

A PRP separator-concentrator can include a PRP concentrator that comprises a concentration chamber having a floor for supporting desiccating beads and a wall with at least one opening covered or closed with a screen, the screen having openings that are sized to retain the desiccating beads in the concentration chamber, the concentration chamber being surrounded by an outer wall with a sloped floor secured thereto, the sloped floor including at its center, a PRP concentrate sump.

A PRP separator-concentrator can include a stationary bead rake that is secured to a stationary tube and extends outward therefrom, the rake having distal ends that are spaced at a distance from the upright screen supports. The concentrator chamber can contain sufficient desiccating beads to remove enough water to produce a product having from above one time up to about four times a base concentration or higher.

A process for separating platelet rich plasma from blood comprising a plasma, erythrocytes and platelets employs a device comprising cylindrical inner wall having a top edge and a central axis surrounded by a depth filter having a capacity to receive all of the erythrocytes in the blood but insufficient to receive all of the plasma in the blood, the inner surface of the inner wall having an angle of from about 0.2 degrees, including about 0.2 to about 20 degrees, such as about 0.2 degrees to about five degrees, from the central axis of the inner wall. The process can include: a) spinning the inner cylinder about its central axis at a speed that centrifugally separates the erythrocytes from the plasma and platelets and causes the erythrocytes to slide up the inner surface; b) continuing spinning for a time sufficient to allow the erythrocytes to flow up the inner surface and over the top edge into the depth filter, leaving platelet enriched plasma behind in the inner cylinder; c) slowing or discontinuing the spinning to permit the platelet enriched plasma to flow to the bottom of the inner cylinder.

The inner surface of the inner wall can be segmented by radially extending plates into separation zones, the plates maintaining substantially balanced distribution of the blood in the separation zones during rotation of the separation chamber, thereby reducing vibration and erythrocyte displacement from the depth filter. The rotational speed of the separation chamber can be accelerated to centrifugal speeds at a rate that allows balanced distribution of blood in the separation zones. After the centrifuging is complete, the rotation speed of the separation chamber can be decelerated to below centrifugal speeds at a rate that allows balanced distribution of the PRP in the separation zones. The acceleration and deceleration process can reduce vibration and erythrocyte displacement from the depth filter. The process can include separating platelet rich plasma from blood according to the above process and then concentrating the platelet rich plasma by contacting the platelet rich plasma with desiccating beads in a rotating concentrating chamber while the beads are stirred with a rake to form a platelet rich plasma concentrate.

When the concentrating chamber includes an outer screened cylinder confining the desiccating beads, the platelet rich plasma concentrate can be separated from the beads by rotating the concentrating chamber about its central axis at a speed that separates platelet rich plasma concentrate from the beads.

According to various embodiments, a process for preparing platelet rich plasma concentrate for wound healing, at least about 85 volume percent of the hematocrit value of the blood and less than a major portion of the erythrocyte depleted platelet rich plasma can remain after the erythrocyte fraction is retained by the depth filter.

According to various embodiments, a process for preparing platelet rich plasma concentrate for hemostasis, at least about 97 volume percent of the hematocrit value of the blood and less than a major portion of the erythrocyte free platelet rich plasma can remain after the erythrocyte separation is retained by the depth filter.

According to various embodiments, a process for preparing platelet rich plasma concentrate for all applications, at least about 99 volume percent of the hematocrit value of the blood and less than a major portion of the erythrocyte free platelet rich plasma can remain after the erythrocyte separation is retained by the depth filter.

According to various embodiments, a process for preparing platelet rich plasma concentrate for all applications, about 100 volume percent of the hematocrit value of the blood and less than a major portion of the erythrocyte free platelet rich plasma can remain after the erythrocyte separation is retained by the depth filter.

In the above processes for preparing platelet rich plasma concentrate for hemostasis, optionally less than a significant portion of the erythrocyte free platelet rich plasma remaining after the erythrocyte separation is retained by the depth filter.

A Platelet Rich Plasma separator assembly comprising a cylindrical outer wall closed at the top by an upper plate and closed at the bottom. The outer wall has an inner surface; a cylindrical inner wall concentric with the cylindrical outer wall and having a top edge and a bottom. The inner wall has a central axis. The bottom of the inner wall is closed by a sloped bottom plate having a central opening, the bottom plate having an upper surface sloped down to a central opening. The top edge of the inner wall terminates at a distance from the upper plate to define an annular erythrocyte passageway therebetween. The inner wall has an outer surface and an inner surface that slopes radially inward from its top edge to its bottom at an angle of from about 0.2 degrees, including about 0.2 to about 5 degrees with the central axis of the inner wall. A cylindrical depth filter is positioned between the inner surface of the outer wall and the outer surface of the inner wall in communication with the inner wall through the erythrocyte passageway. The device can be combined with a PRP concentrator assembly. The concentration assembly has a PRP concentration sump; an axially concentric rigid stationary outlet tube secured to the housing and extending through the PRP separation assembly to the PRP concentrate sump; and the PRP separation assembly is attached to and positioned above the PRP concentration assembly to form a combined separator-concentrator assemblage that is rotatable about the outlet tube.

BRIEF DESCRIPTION OF THE DRAWINGS

FIG. 13 is a front plan view of the valve assembly of the separation-concentration assembly shown in FIG. 4.

FIG. 14 is an exploded, isometric view of the valve assembly of FIG. 13.

FIG. 15 is a cross-sectional view of the bottom bucket subassembly shown in FIG. 4, taken along the central axis.

FIG. 16 is an enlarged cross-sectional view of the motor drive connector shown in FIG. 15.

DETAILED DESCRIPTION

The apparatus and method can prepare a PRP concentrate that combines enhanced platelet levels in a plasma concentrate, in which the fibrinogen levels have not been significantly denatured. The product can combine the sealant and properties of the plasma concentrates for use in certain types of surgery with the healing properties provided by elevated platelet levels.

Figure 1:
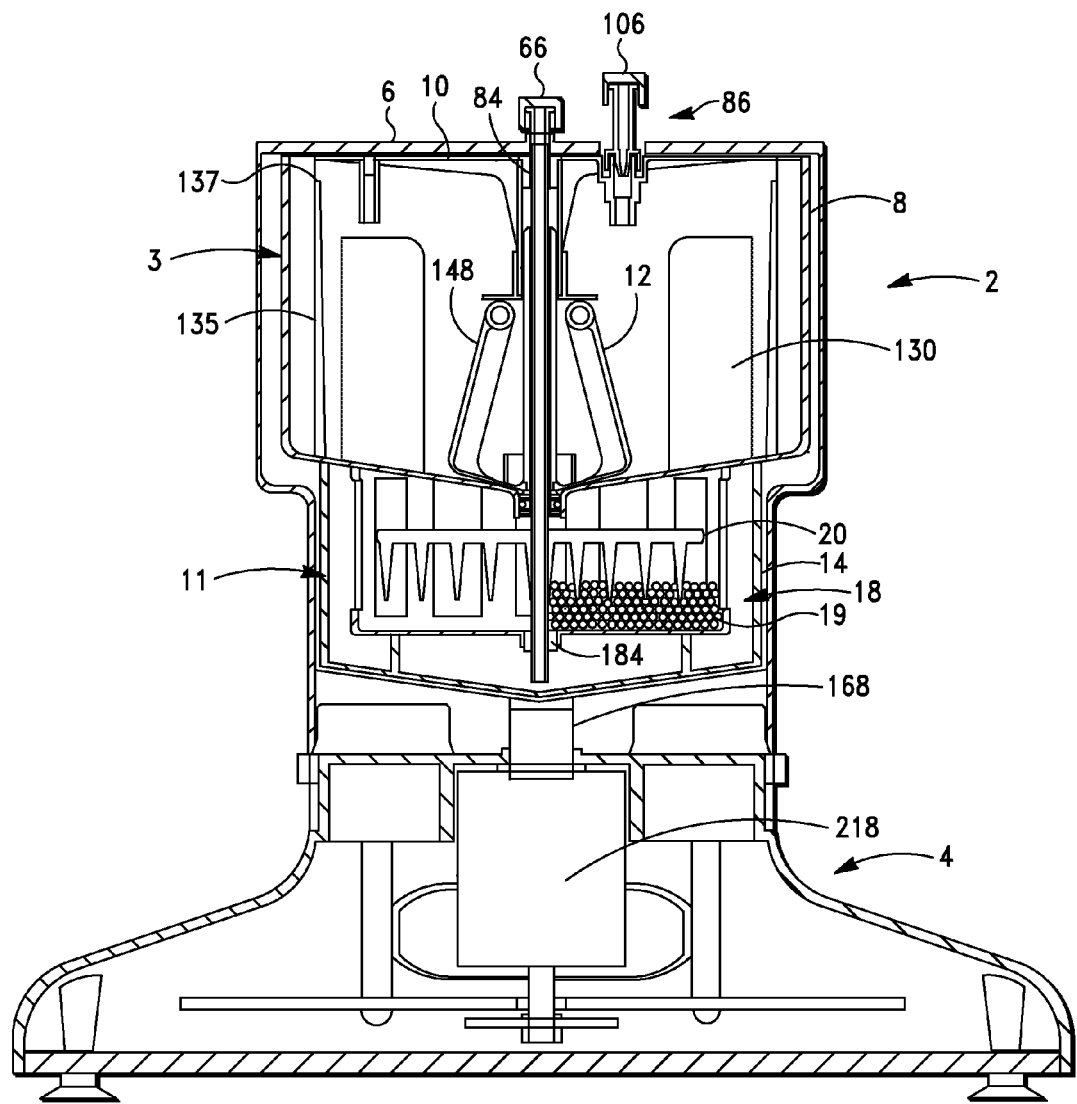
FIG. 1 is a cross-sectional view of a disposable separation and concentration assembly and a permanent drive assembly, with desiccating beads shown in only half of the concentration subassembly.

FIG. 1 is a cross-sectional view of a disposable separation and concentration assembly and a permanent drive assembly, with desiccating beads shown in half of the concentration subassembly. Details of the sub-sections of this assembly are hereinafter described in conjunction with more detailed drawings.

The upper housing 2 is described in greater detail hereinbelow in conjunction with FIGS. 2 and 3.

Figure 22:
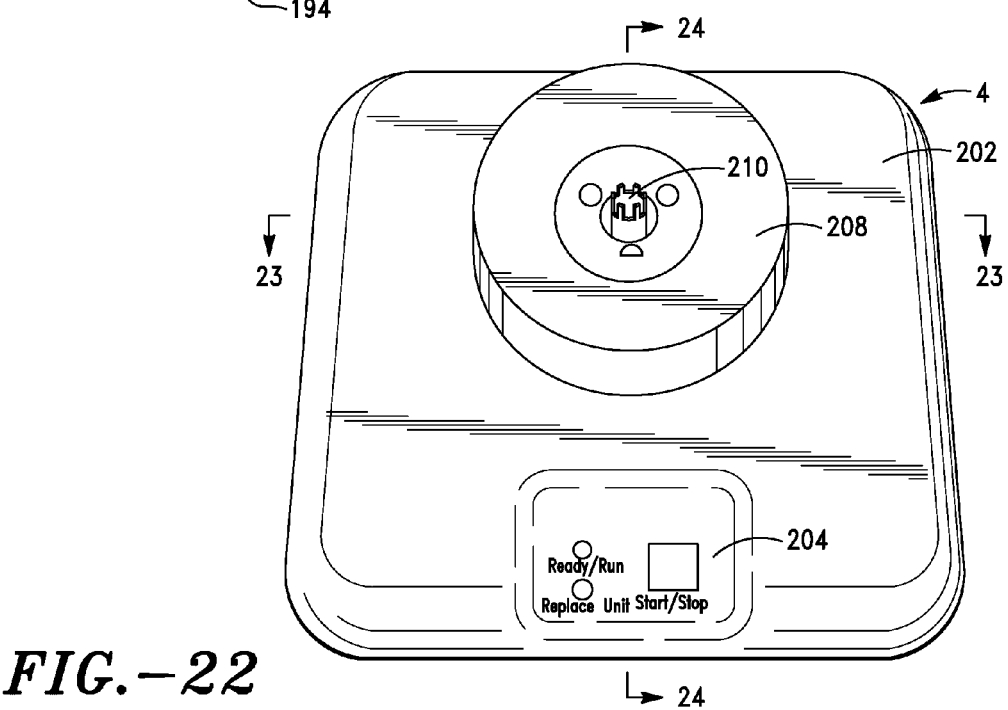
FIG. 22 is a perspective view of the motor drive assembly of this invention.
Figure 23:
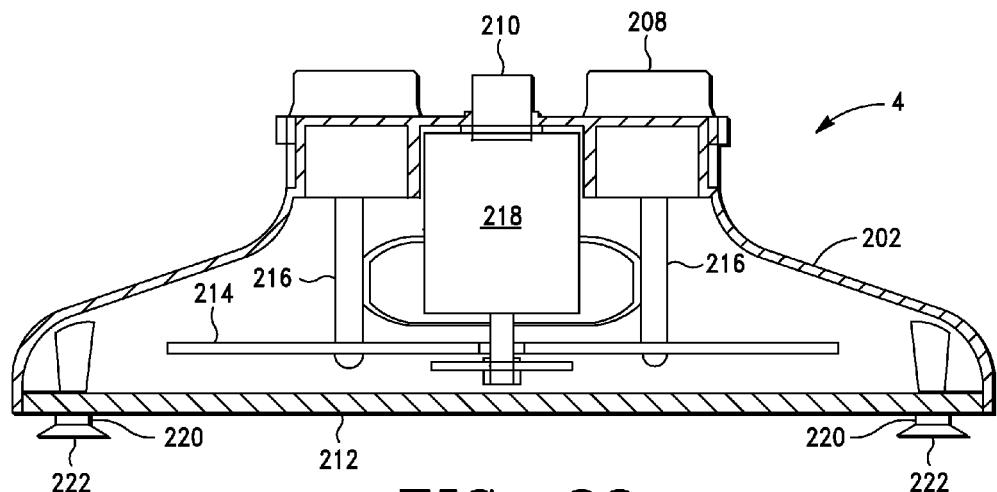
FIG. 23 is a cross-sectional view of the motor drive assembly of FIG. 22 taken along the line 23-23.
Figure 24:
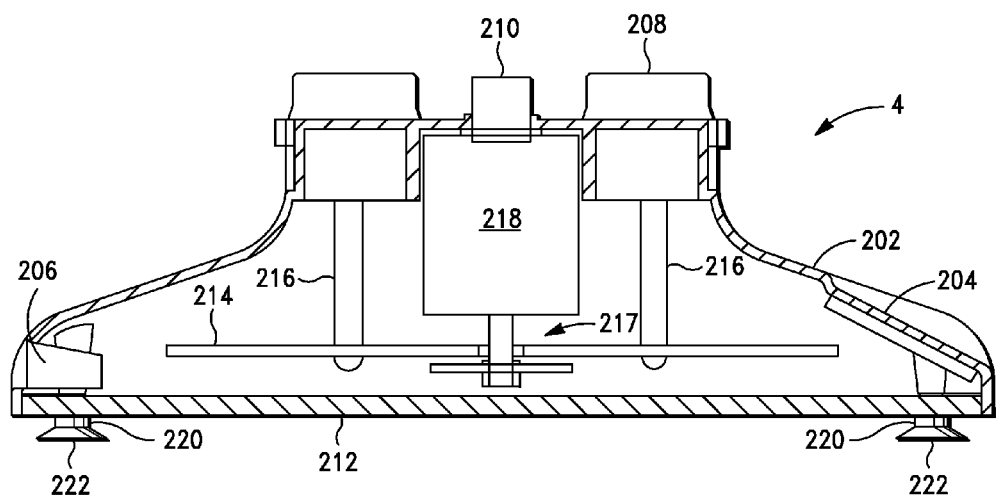
FIG. 24 is a cross-sectional view of the motor drive assembly of FIG. 22 taken along the line 24-24.

The motor drive subsystem 4 is described together with the motor drive system in conjunction with FIGS. 22-24.

Figure 4:
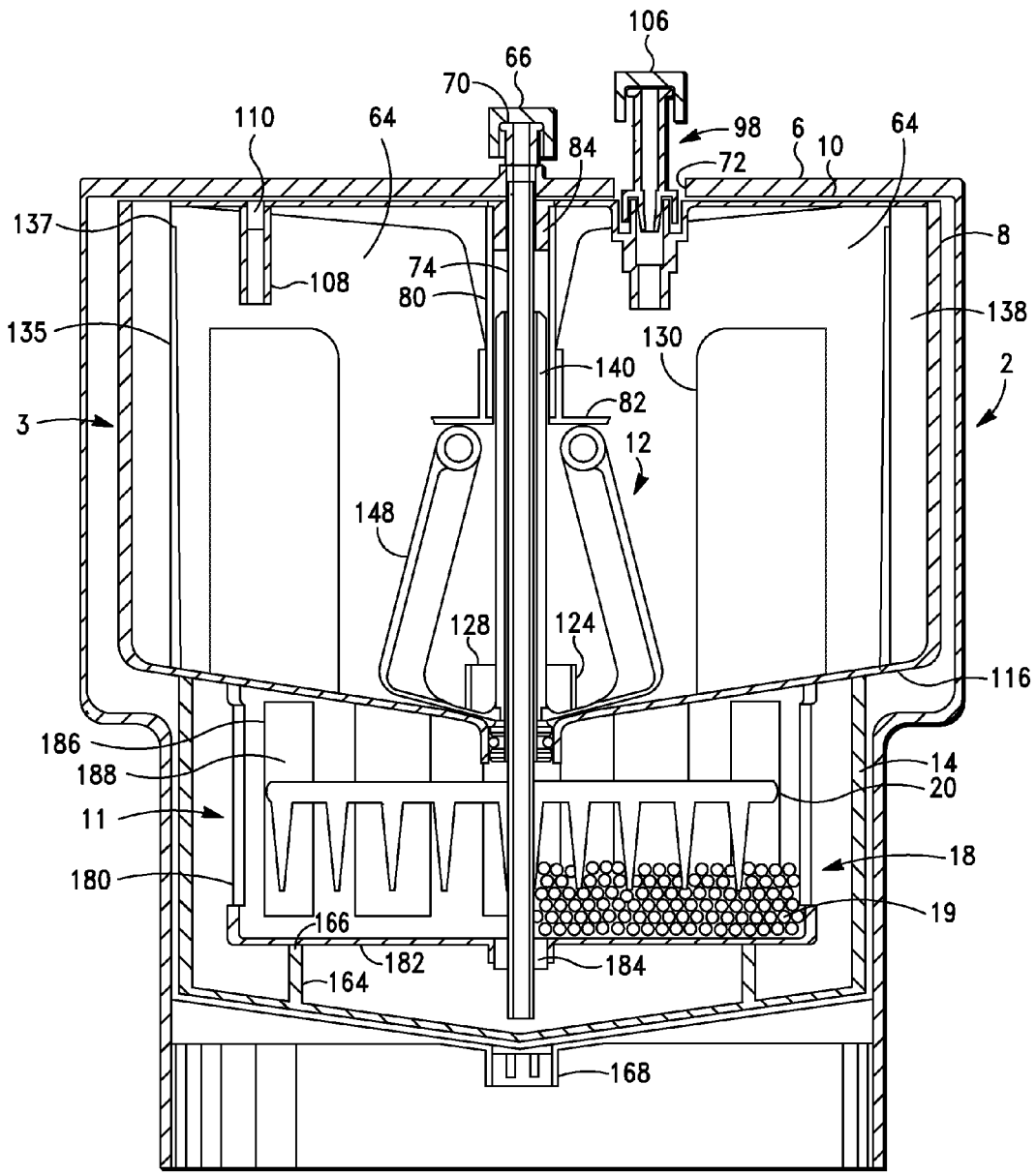
FIG. 4 is a cross-sectional drawing of the separation-concentration sub-assemblies shown in FIG. 1.

The separation system 3 enclosed in the upper housing 2 is described in greater detail with regard to FIG. 4. The separation system comprises a combination of subsystems including the outer cap subassembly 6 described in greater detail with respect to FIGS. 5-7; a top bucket 8 described in greater detail with regard to FIGS. 8 and 9; a sample inlet subassembly shown in FIG. 10; a top bucket cap subassembly 10 described in greater detail with respect to FIGS. 11 and 12; and a valve subassembly 12 described in greater detail with respect to FIGS. 13 and 14.

Figure 17:
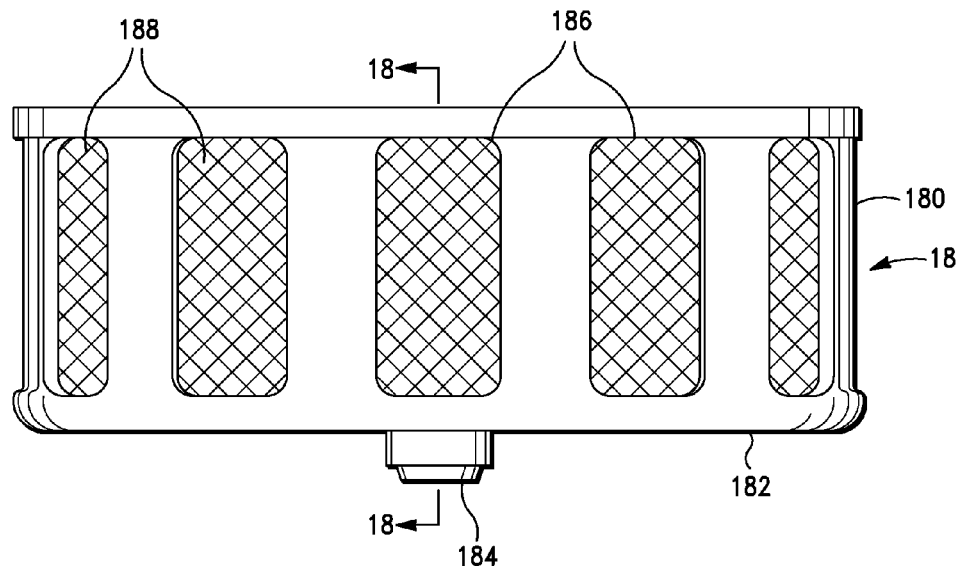
FIG. 17 is a front plan view of the basket subassembly of the separation-concentration assembly shown in FIG. 4.
Figure 18:
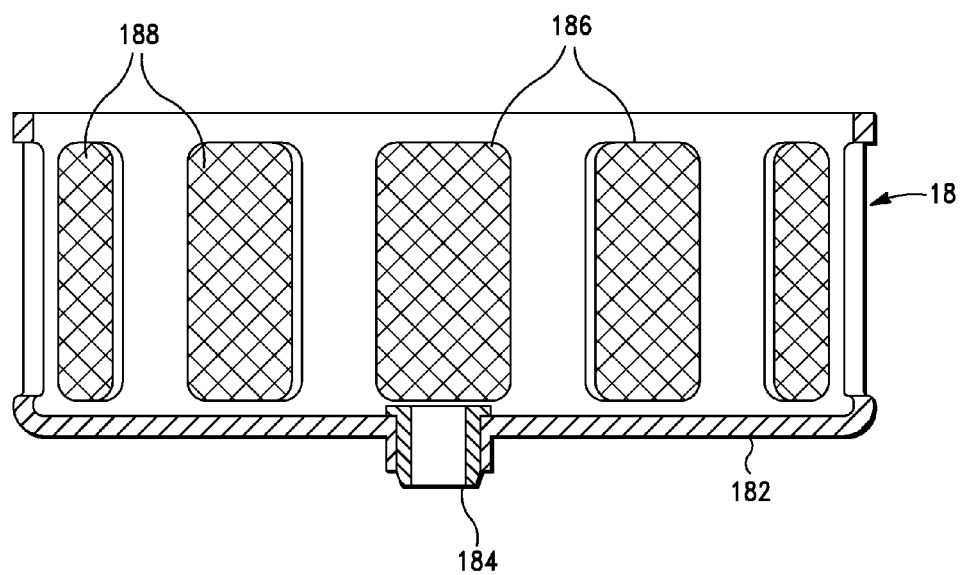
FIG. 18 is a cross-sectional view of the basket subassembly of FIG. 16, taken along the line 18-18.
Figure 20:
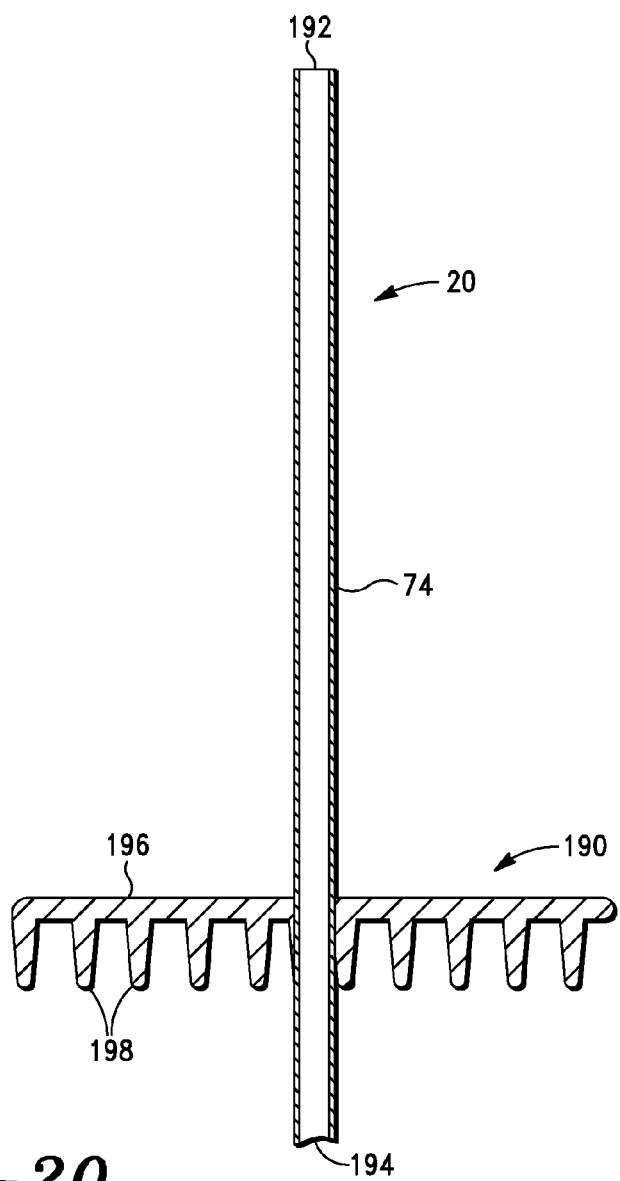
FIG. 20 is a cross-sectional view of the mixer assembly of FIG. 19, taken along the line 20-20.
Figure 19:
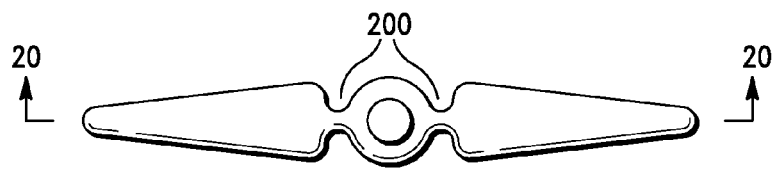
FIG. 19 is a top plan view of the mixer assembly of the separation-concentration assembly shown in FIG. 4.
Figure 21:
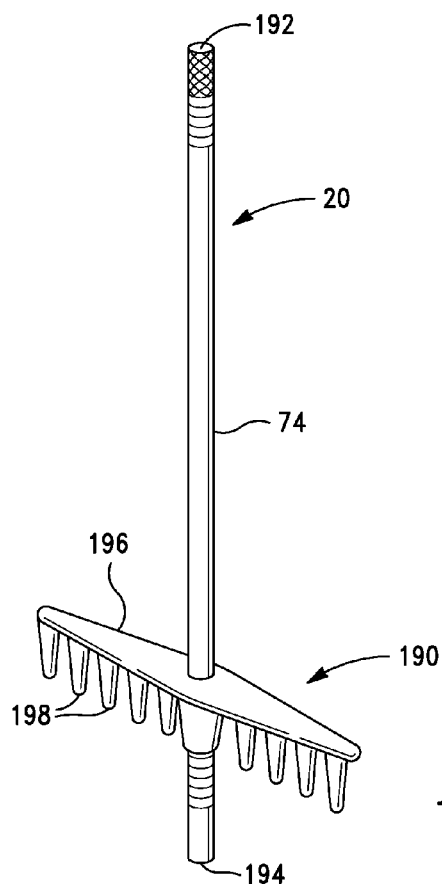
FIG. 21 is an isometric view of the mixer assembly of FIGS. 19 and 20.
Figure 26:
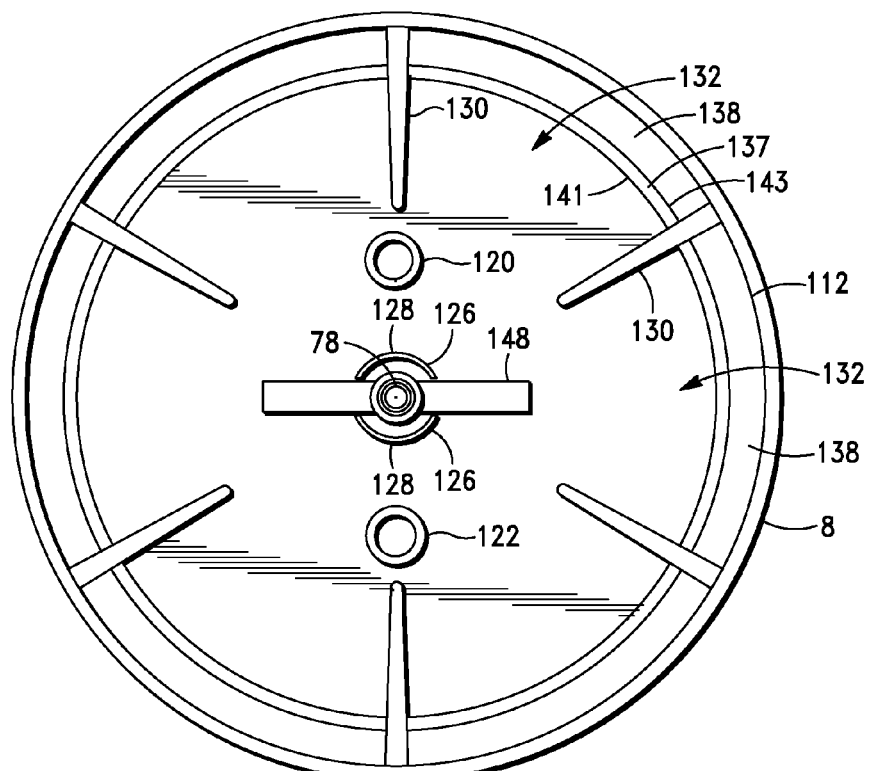
FIG. 26 is a cross-sectional view of the upper bucket and valve assembly of FIG. 21, taken along the line 26-26.

The concentrating system 11 includes a lower bucket 14 and drive connector 16, described in greater detail with regard to FIGS. 15 and 26; a basket subassembly 18 described in greater detail with regard to FIGS. 17 and 18; and a mixer assembly described in greater detail with regard to FIGS. 19 to 21.

Figure 2:
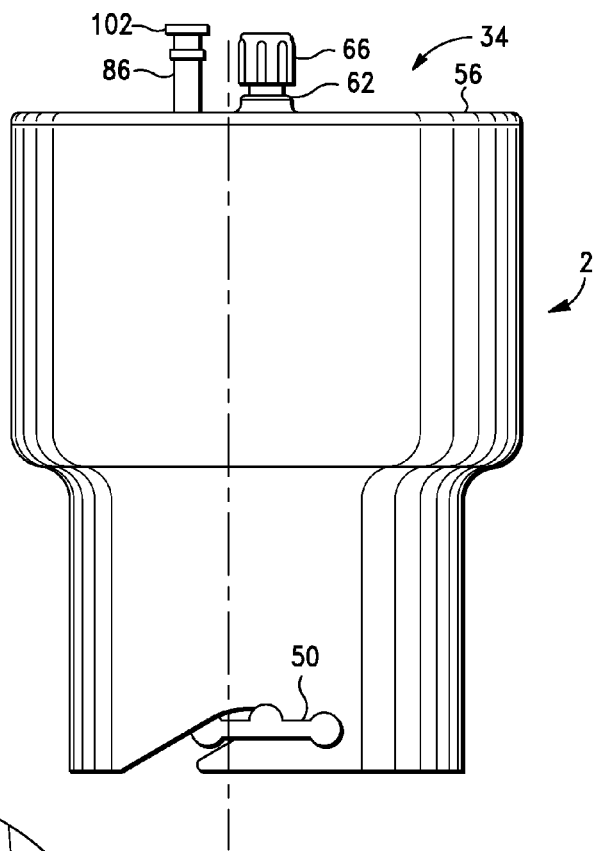
FIG. 2 is a front plan view of the outer housing of the separation-concentration assembly of this invention.
Figure 3:
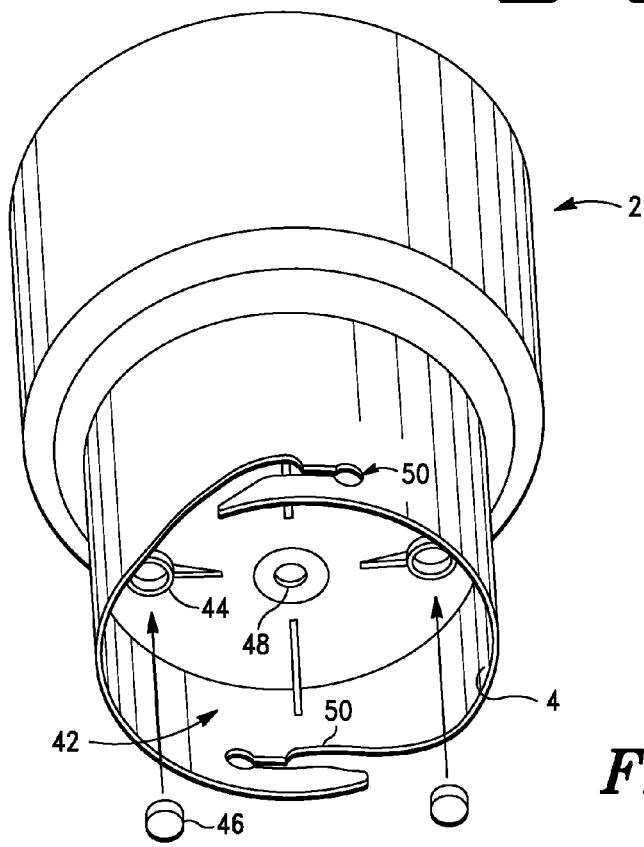
FIG. 3 is a perspective view of the outer housing of FIG. 2 showing details of the motor assembly connector.

FIG. 2 is a front view of the outer housing of the separation-concentration assembly of this invention, and FIG. 3 is a perspective view of the outer housing of FIG. 2 showing details of the motor assembly connector.

The upper housing 2 isolates the sterile separation and concentration systems shown in FIG. 1. The upper portion of the outer housing 2 is sealed with an outer cap subassembly 34 having a blood inlet tube 86 and a PRP concentrate outlet port 62 and cap 66. Referring to FIG. 3, the lower assembly connector has a drive recess 42 shaped to engage the motor subassembly, and with spacer receptors 44 for holding spacers 46. The outer housing 2 and its enclosed separation components are a disposable unit and can be used with a permanent drive assembly shown in FIGS. 1 and 22 to 24. The lower assembly includes an axially concentric motor drive receptor 48 and a plurality of tapered engagement and locking slots 50 that engage with corresponding mounting projections of the motor drive assembly (not shown).

FIG. 4 is a cross-sectional drawing of the separation-concentration sub-assemblies shown in FIG. 1. The outer housing 2 encloses an upper separation subassembly 3 and a lower concentration subassembly 11.

Figure 6:
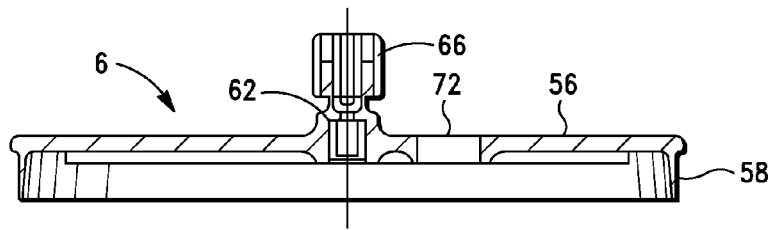
FIG. 6 is a cross-sectional view of the outer cap subassembly shown in FIG. 5, taken along the line 6-6.
Figure 5:
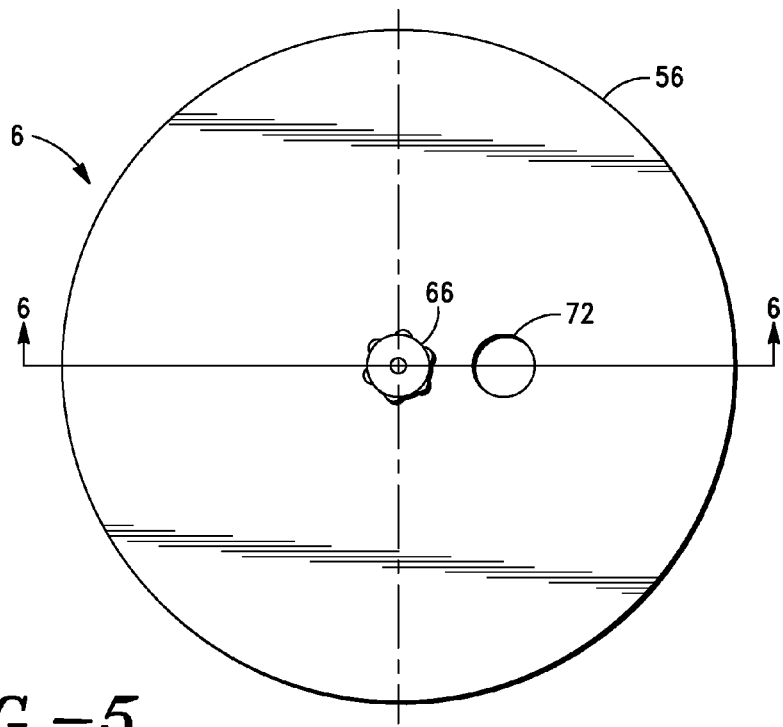
FIG. 5 is a top view of the outer cap subassembly of the separation-concentration assembly shown in FIG. 4.
Figure 7:
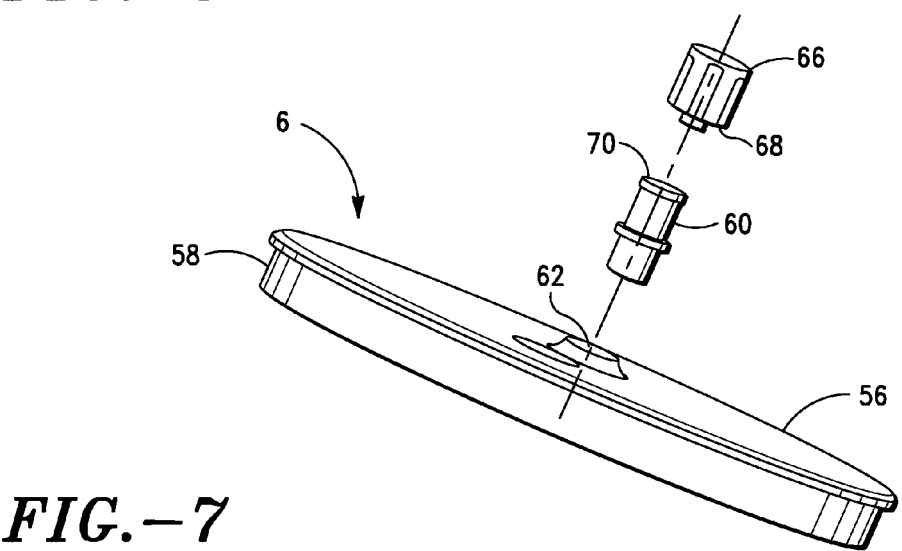
FIG. 7 is an exploded, isometric view of the outer cap subassembly shown in FIG. 5.

The top of the outer housing 2 is closed with outer cap subassembly 6 shown in greater detail with regard to FIGS. 5-7. The outer cap subassembly 6 comprises a circular cap 56 with an annular flange 58 extending downward for securing it to the top of the upper housing 2. Concentrate outlet conduit 60 passes through an outlet conduit hole 62 in the center of the plate 56, extending through the plate and communicating with the separation chamber 64 (FIG. 4). Circular cap 66 has a central receptor 68 that engages with a Luer fitting 70 on the upper end of the outlet conduit 60 to maintain a sterile closure during the separation process.

An inlet port hole 72 is positioned in the circular cap 56, spaced from the central axis. The inlet port hole 72 is sized to engage the exterior inlet conduit 74 shown in FIG. 4.

The Luer fitting 70 is provided to engage an empty applicator syringe for removing platelet rich plasma concentrate product according to this invention. The lower end of the concentrate outlet conduit 60 constitutes a receptor for receiving the upper end of rigid tube 74 (FIG. 4).

Figure 8:
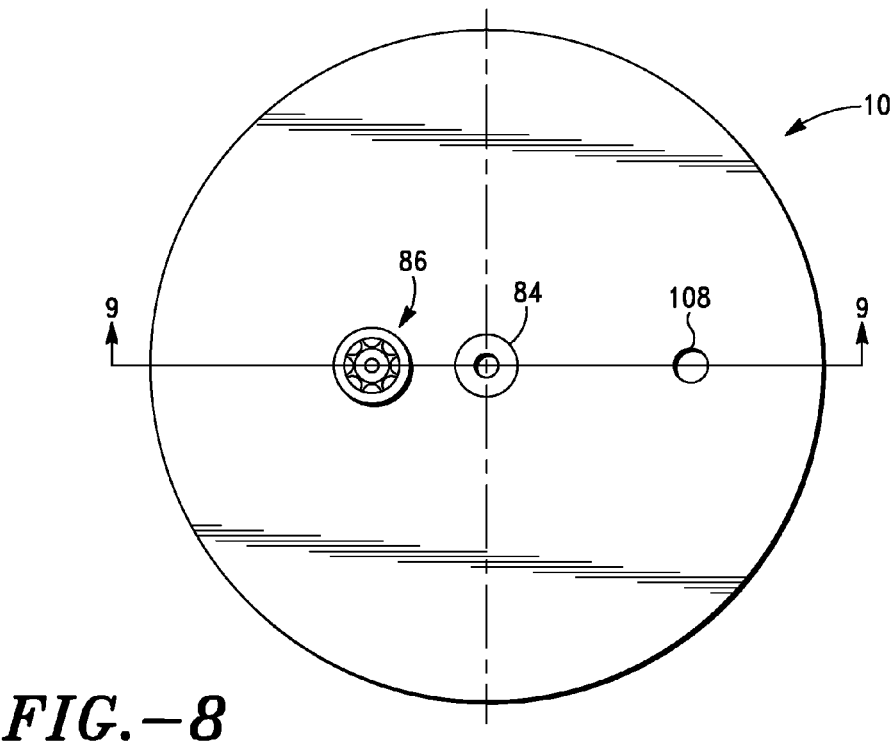
FIG. 8 is a top view of the top bucket cap subassembly of the separation-concentration assembly shown in FIG. 4.
Figure 9:
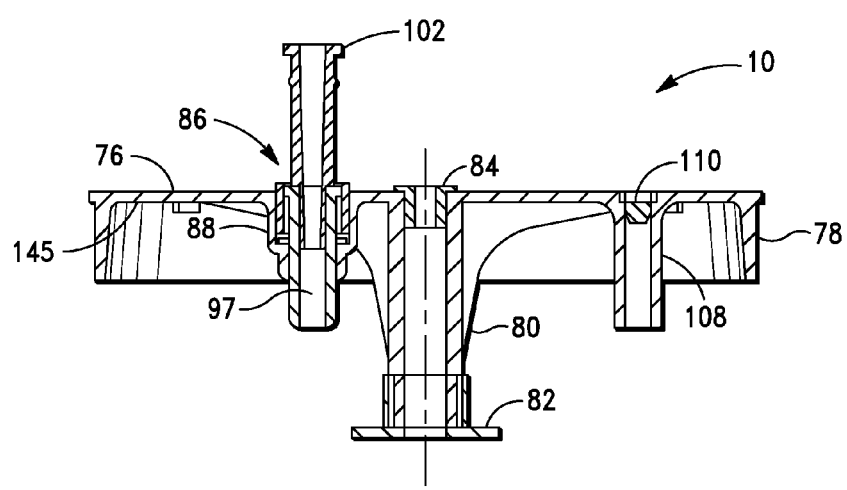
FIG. 9 is a cross-sectional view of the top bucket cap subassembly shown in FIG. 8, taken along the line 9-9.
Figure 10:
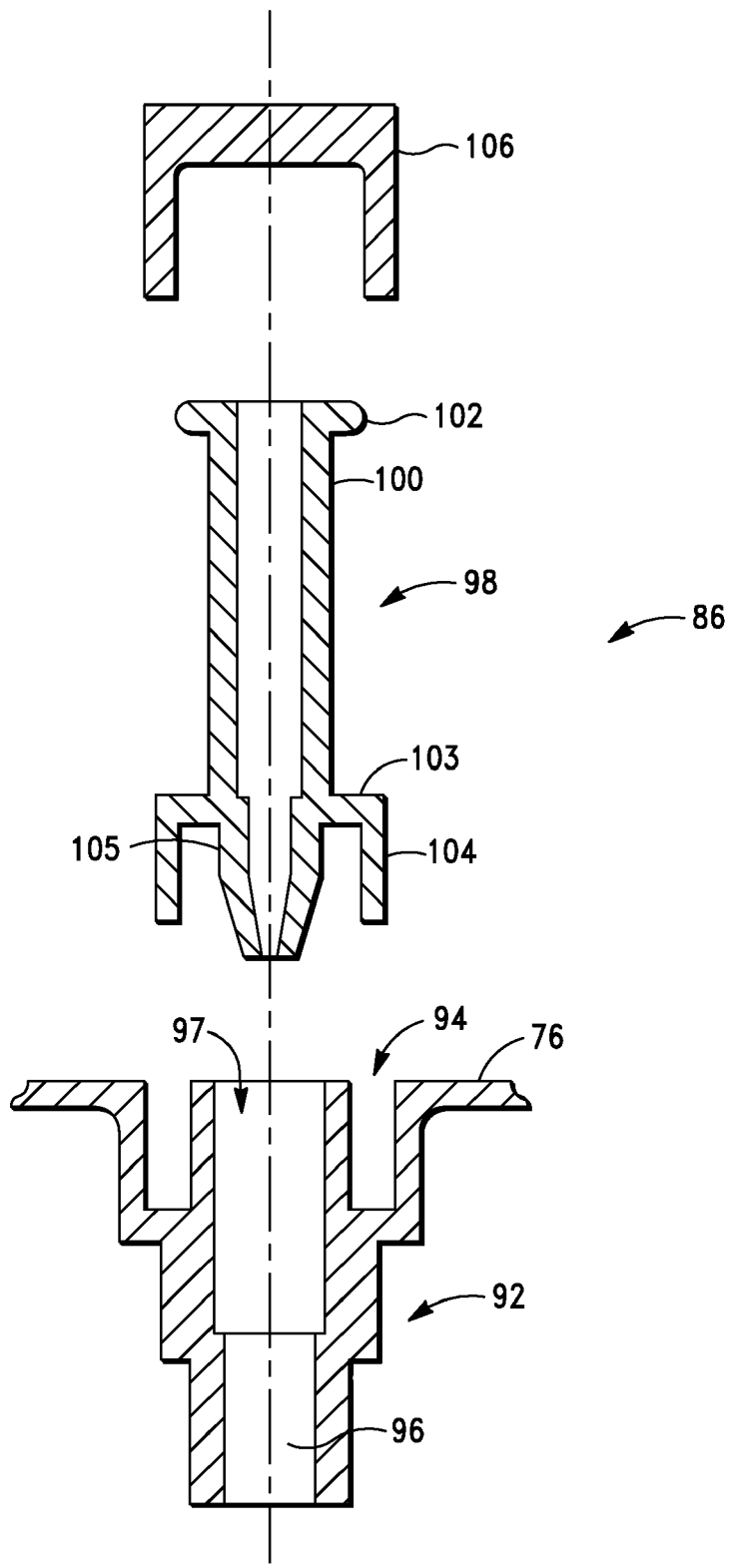
FIG. 10 is an exploded view of the sample inlet subassembly.

The bucket cap 10 shown in FIG. 4 is described in greater detail with regard to FIGS. 8-10. FIG. 8 is a top view of the top bucket cap subassembly 10 of the separation-concentration assembly shown in FIG. 4, and FIG. 9 is a cross-sectional view of the top bucket cap subassembly shown in FIG. 10, taken along the line 9-9. The cap subassembly 10 closes the top separation bucket 8 shown in greater detail with respect to FIGS. 11 and 12. The top bucket cap 10 comprises a circular plate 76 with a connecting flange 78 that extends downward from the lower edge of plate 76. The upper plate 6 is fixed to the outer housing 2 (FIG. 4) and is stationary during the separation and concentration processes. Top bucket cap 10 is secured to the top bucket 8 during the separation and concentration processes.

The circular cap 10 has an axially concentric hole with a valve assembly guide tube 80 extending downwardly therefrom. The lower end of the guide tube 80 has a valve assembly stop flange 82 secured thereto. The upper end of the guide tube 80 supports sleeve bearing 84. The sleeve bearing 84 can be formed of materials that are wear resistant and can be sterilized in an appropriate manner. Materials that can be used for the sleeve bearing include polyaryletherketone such as TECAPEEK™ Classix™, and the like.

The circular cap 10 has a sample inlet subassembly 86 that aligns with the hole 72 in the circular cap 56 (FIG. 5).

FIG. 10 is an exploded view of the sample inlet subassembly 86. The sample inlet subassembly 86 comprises an inlet tube 92 mounted in the plate 76, the top of the inlet tube 92 including an annular receptor 94. A sterile filter 96 can be positioned in the lower end of the passageway 97 of tube 92.

The subassembly 86 includes a removable inlet tube 98. Inlet tube 98 comprises a central tube 100 having at its upper end an integral Luer fitting 102. At an intermediate level of the tube 100, an annular plate 103 extends outward from the tube 100. An integral cylindrical flange 104 extends downward from the outer edge of the plate 103. The flange 104 is sized to engage the receptor 94. The lower end 105 of the tube 100 is sized to engage the upper end of the passageway 97.

The inlet tube is provided with a cap 106 that engages the Luer fitting 102 to provide a sterile closure of the removable inlet tube 98 prior to use, such as during shipment and handling.

The inlet tube 98 in passing through the hole 72 in the stationary circular cap 56 locks the separation and concentration subassemblies against rotation during shipment and storage. After the patient blood is introduced into the top bucket 8 (FIG. 4) through the inlet subassembly 86, the inlet tube 98 is removed, unlocking the separation and concentration subassemblies 3 and 11 from the stationary circular cap 6, freeing them for rotation about the central tube 74.

A sterile breathing tube 108 is secured to the circular plate 76 to permit air flow from the separation chamber 64 when blood is introduced and to permit air movement into the system when platelet-rich concentrate is removed from the concentrating system 11, as described in greater detail hereinafter. Sterile air filter 110 in breathing tube 108 (FIG. 9) prevents entrance of micro-organisms into the interior of the separation chamber, preserving sterility.

Figure 11:
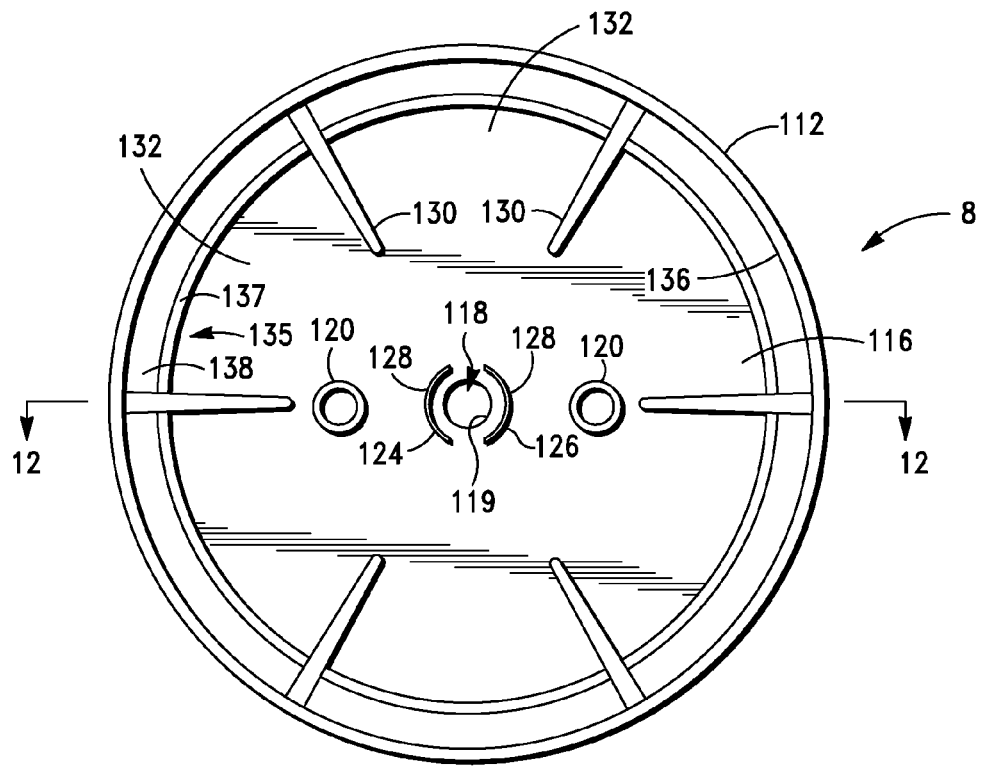
FIG. 11 is a top plan view of the top bucket subassembly of the separation-concentration assembly shown in FIG. 4.
Figure 12:
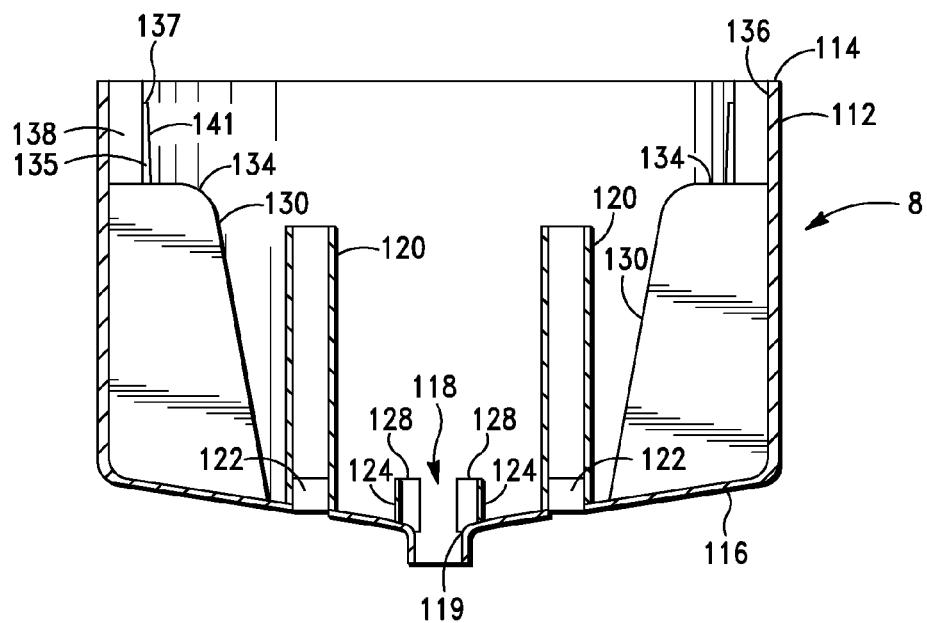
FIG. 12 is a cross-sectional view of the top bucket subassembly of FIG. 11, taken along the line 12-12.

The top bucket subassembly in FIG. 4 is shown in detail in FIGS. 11 and 12. FIG. 11 is a top view of the top bucket subassembly 10 of the separation-concentration assembly shown in FIG. 4, and FIG. 12 is a cross-sectional view of the top bucket subassembly of FIG. 11, taken along the line 12-12. The top bucket subassembly 10 comprises a cylindrical outer wall 112 having a top edge 114 that is secured to the inner surface of the flange 58 of the upper bucket cap 10. The lower end of the cylindrical outer wall 112 is closed with integral sloped floor plate 116 with a central passageway 118 that constitutes a central flow passageway for separated platelet-plasma. The inner wall surface of the passageway 118 constitutes a valve seat 119 for the valve assembly described in greater detail hereinafter with respect to FIGS. 13 and 14. Spaced from the central passageway 118 and secured to the floor plate 116 are vent columns 120 with filters 122 in their bottom. The columns 120 serve as vents allowing movement of air from the concentration subassembly into the separation chamber when liquid flows through downward through the central passage 118, as is explained hereinafter. Filters 122 prevent escape of hydrogel beads from the basket subassembly 18 through the vent columns 120 during transport or handling of the device of this invention. Surrounding the central passageway 118 and secured to the upper surface of the tapered floor plate 116 are upwardly extending abutment plates 124, each having an upper valve arm abutment surface 128.

Figure 12A:
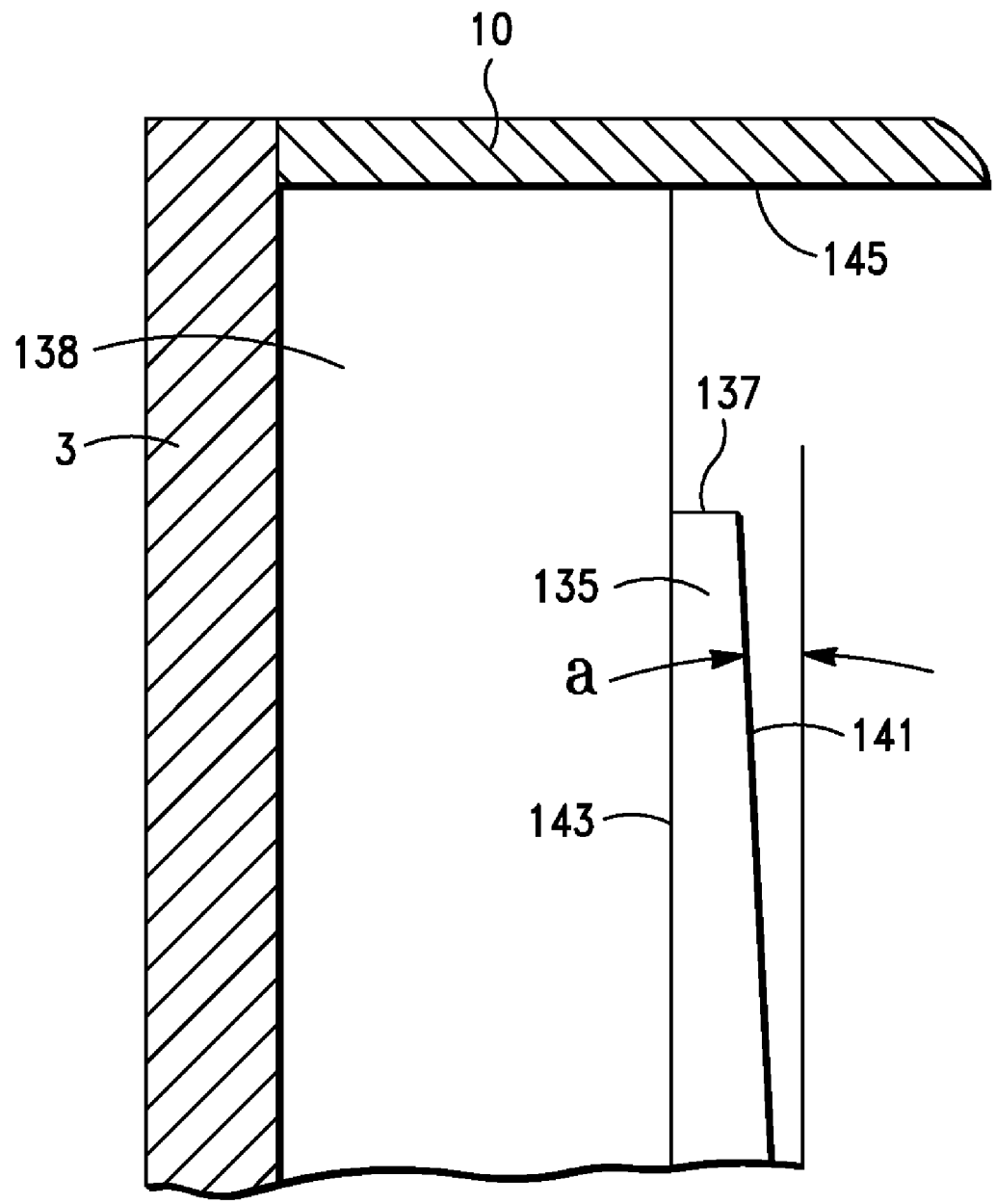
FIG. 12A is a cross-sectional exploded sectional view of an upper portion of the separation-concentration sub-assemblies shown in FIGS. 11 and 12.

Referring to FIG. 12A, the separation zone can be further limited by an inner cylinder 135 extending from the upper surface of the bottom plate 116 upward to an upper lip 137. The inner surface of the cylinder 141 can have a slope "a" of from about 0.2 degrees, including between about 0.2 to about 5 degrees and optionally between about 0.2 to about 2 degrees relative to the central axis. This slope can be selected to facilitate flow of erythrocytes along the surface and beyond the lip 137 into the depth filter 138. Because the slope can be selected to be small, the separation of platelets trapped by the erythrocytes is facilitated, leaving a maximum quantity of platelets suspended in the plasma phase.

The depth filter 138 can extend from the bottom surface 145 past top edge 137 to completely block the opening defined by the top lip 137 and the bottom surface 145. This can be provided to assist in preventing the return of erythrocytes to the plasma from the volume between the outer cylinder 3 and the inner cylinder 135. In various embodiments, the depth filter can extend to the bottom plate 116 which can insure complete capture of erythrocytes. In various embodiments, if the space between the upper edge 137 and lower surface 145 is sufficiently small and risk of a return of a small amount of erythrocytes to the plasma is acceptable, the depth filter can be omitted.

A plurality of radially inwardly extending separation plates 130 are secured to the inner surface of the cylindrical outer wall 112 and the sloped floor plate 116. Each adjacent pair of these plates defines a separation zone 132. The plates 130 can be evenly spaced around the cylindrical outer wall to provide a balanced subassembly. They can be in matched, opposed pairs, for example the three matched sets as shown in FIG. 11. The top edge 134 of each of the separation plates 130 is spaced at a distance below the top edge 114 to permit overflow of blood in order to achieve an even distribution of blood between each the separation zones 132 during the spin acceleration stages and during the spin deceleration stages. This can maintain balance and minimize vibration of the rotating assembly.

The space between the interior surface 136 of the cylindrical outer wall segments and the outer surface 143 of the inner cylinder in each of the each separation zones 132 contains the open-cell foam segment or depth filter segment 138. The foam segments 138 have pores and passageways sized to allow infiltration of erythrocytes into the foam and subsequent entrapment of erythrocytes during the high speed centrifugation of the separation stage. The pores and passageways are sized to retain entrapped erythrocytes thereafter when the spinning slows or stops and the erythrocyte-free platelet-plasma suspension flows downward through the opening 118.

The distance between the lip 137 and the lower surface 145 of the upper plate is sufficient to permit flow of all erythrocytes into the depth filter 138 during the separation phase. It can be between about 0.02 and about 50 mm, such as about 0.02 mm to about 10 mm, or another dimension that facilitates a selected amount, such as complete erythrocyte removal while trapping a minimum portion of the platelets.

The provision of the inner sloped cylinder can increase the proportion of platelets remaining in the plasma.

FIG. 13 is a front view of the valve assembly 12 of the separation-concentration assembly shown in FIG. 4, and FIG. 14 is an exploded, isometric view of the valve assembly of FIG. 13. The valve assembly 12 comprises a central tube 140, the lower end constituting a valve face 142. The valve face 142 comprises an annular receptor 144 that receives and holds an O-ring 146. The outermost surface of the O-ring 146 can be sized to form a sealing engagement with the valve seat 119 (See FIGS. 11 and 12).

The valve assembly 12 includes two opposed centrifugal arms 148 secured to the tube 140 above the valve face 142. Each centrifugal arm 148 has a flexible portion 150 adjacent the tube 140 and a rigid arm portion 152. The distal end of the rigid arm portion 152 includes a weight receptor 154 in which a weight 156 is secured to provide additional weight to the end of the rigid arm portion. Operation of the valve assembly is described hereinafter with respect to FIGS. 25-31.

The lower bucket 14 in FIG. 4 is shown in detail in FIGS. 15 and 16. Referring to FIG. 15, the lower bucket 14 has a cylindrical sidewall 158 and a sloped bucket bottom 160, the lower portion of which forms a platelet-plasma concentrate sump 162 in which concentrated platelet and plasma concentrate collects. A plurality of basket supports 164 extend upward from the top surface of the slopped bucket bottom 160, the top surfaces 166 of which support a concentrating basket subassembly 18 described hereinafter with regard to FIGS. 17 and 18.

An axially concentric drive receptor 168, shown in detail in FIG. 16, is secured to the bottom surface of the bucket bottom 160. The drive connector receptor 168 can have any configuration that will releasably couple with a suitably configured motor drive connector. In the configuration shown in FIGS. 15 and 16, the drive receptor 168 comprises an outer cylinder 170 and a plurality of ridges 172, each ridge having a tapered leading engagement surface 174, an abutment surface 176 and an upper plate 178. The upper plate 178 transmits the torque from the drive motor (described hereinafter with respect to FIGS. 22-24) to the lower bucket bottom 160 and from there to the concentrating and separating subassemblies, all of which are secured together to form a unitary rotatable assembly.

FIG. 17 is a front view of the basket subassembly 18 of the separation-concentration assembly shown in FIG. 4, and FIG. 18 is a cross-sectional view of the basket subassembly of FIG. 17, taken along the line 18-18. The basket subassembly 18 comprises a cylinder 180 secured to a circular floor plate 182. A slip bearing 184 is positioned in the axial center of the circular plate 182 for engaging the rigid tube 74 (FIG. 4). The slip bearing 184 can be formed of a material that is wear resistant and can be sterilized in an appropriate manner, these materials can be the same or similar to those that form the sleeve bearing 84. The cylinder 180 has an array of windows or openings 186 around its circumference, each window closed or coveted with a fine screen 188 having a mesh size sufficiently small to prevent escape of hydrogel beads 19 (FIGS. 1 and 4) from the basket during spinning.

FIG. 19 is a top view of the mixer assembly of the separation-concentration assembly shown in FIG. 4. FIG. 20 is a cross-sectional view of the mixer assembly of FIG. 18, taken along the line 20-20, and FIG. 21 is an isometric view of the mixer assembly of FIGS. 19 and 20. The mixer assembly 20 comprises a rake 190 secured to stationary tube 74. The upper end 192 of the stationary tube 74 is secured to the upper cap subassembly 34 to secure it against rotation. At the lower end 194 of the stationary tube 74 is a port for removal of platelet-plasma concentrate from the sump 162 (FIG. 15). The rake 190 comprises a radially extending spine 196 from which integral rake elements 198 extend downward to an elevation short of the bottom plate 182 of the basket subassembly 18 as shown in FIGS. 4, 17 and 18. The spine 196 can have optional breakaway notches 200 adjacent its center. The notches 200 weaken the spine and direct fracture of the spine 196 at the location of the notches in the event that the pressure produced by contact of the beads 19 with the rake elements 198 during the final centrifugal spin becomes excessive.

The stationary tube 74 extends through the sleeve bearing 184 of the basket subassembly 18 and through the sleeve bearing 84 of the top bucket cap, permitting free rotation of the separating and concentrating assemblies around the stationary tube. The stationary tube 74 is fixed to the outer cap subassembly 6 and the stationary outer housing 2.

FIG. 4 is a comprehensive assemblage of the components shown in FIGS. 5-20.

Concentrating desiccating hydrogel beads 19 fill the lower half of the basket 18 (only one side is shown empty to enable unobstructed viewing of the windows 186 and screen 188 elements (FIGS. 1, 17 and 18).

The concentrating desiccating hydrogel beads 19 can be insoluble beads or disks that will absorb a substantial volume of water and low molecular weight solutes while excluding high molecular weight solutes and particulates and will not introduce undesirable contaminants into the plasma. They can be dextranomer or acrylamide beads that are commercially available (appropriate materials include Debrisan from Pharmacia and BIO-GEL P™ from Bio-Rad Laboratories, respectively). Alternatively, other concentrators can be used, such as SEPHADEX™ moisture or water absorbents (available from Pharmacia), silica gel, zeolites, cross-linked agarose, etc., in the form of insoluble inert beads.

FIG. 4 in conjunction with subassembly FIGS. 5-21 shows the assembly prior to use with the valve assembly 12 secured for shipment by the sleeve 80 into which the valve assembly tube 140 extends and the abutment flange 82 is secured to the bottom of the sleeve 80. The valve face 142 is shown in position against the seat 119. This confines the beads to the basket 18 and prevents escape of beads into the upper separation chamber 64 if the device is inverted or shaken during transport or handling.

The assembly is secured against rotation around the rigid tube 74 by the position of the removable inlet tube 98 in the hole 72 of the stationary outer cap subassembly 6.

The upper edge of the cylinder 180 of the basket assembly 18 is secured against the lower surface of the tapered bottom 116, and the lower surface of the plate 182 is secured against the upper edge surfaces 166 (FIG. 15) of the supports 164.

Thus assembled, the upper separation subassembly 3 and the lower concentration subassembly 11 rotate as a single unit around the fixed tube 74. The upper separation subassembly is positioned on the central tube 74 by the slip bearing 84 through which the fixed tube 74 extends. The lower separation subassembly is positioned on the central tube 74 by the slip bearing 184 through which the fixed tube extends. The rake assembly 20 including the tube 74 remains stationary during rotation of the separation and concentration subassemblies 3 and 11 in the separation and concentration phases, to be described in greater detail hereinafter.

FIG. 22 is a perspective view of the motor drive assembly. FIG. 23 is a cross-sectional view of the motor drive assembly taken along the line 23-23, and FIG. 24 is a cross-sectional view of the motor drive assembly taken along the line 24-24.

The outer shell 202 of the motor housing 4 encloses the motor 218 and supports the control interface 204 and the power connector 206. The separation-concentrating assemblies are supported on the raised annular support surface 208 surrounding the motor connector 210. Motor connector 210 has a configuration that will releasably engage the drive receptor 168 (FIG. 16). The bottom of the housing 22 is closed by support plate 212. A control and power plate 214 for the system is supported by four support struts 216 attached to the underside of the housing shell 202. Plate 214 is a conventional printed circuit or equivalent board with the electronic components of the control and power system for the device, and in its center, a support 217 for the motor 218. The electrical components are connected to the control interface 204 and power connector 206 by conventional wiring circuits (not shown). Four support feet 220 are secured to the bottom of the support plate 212 and provide friction surfaces 222 to secure the device on a laboratory surface.

FIGS. 25-31 illustrate the operation of the valve subassembly during and immediately after the initial separation process. Blood and blood products are omitted from these cross-sectional views to allow an unobstructed view of the valve assembly elements at each stage.

Figure 25:
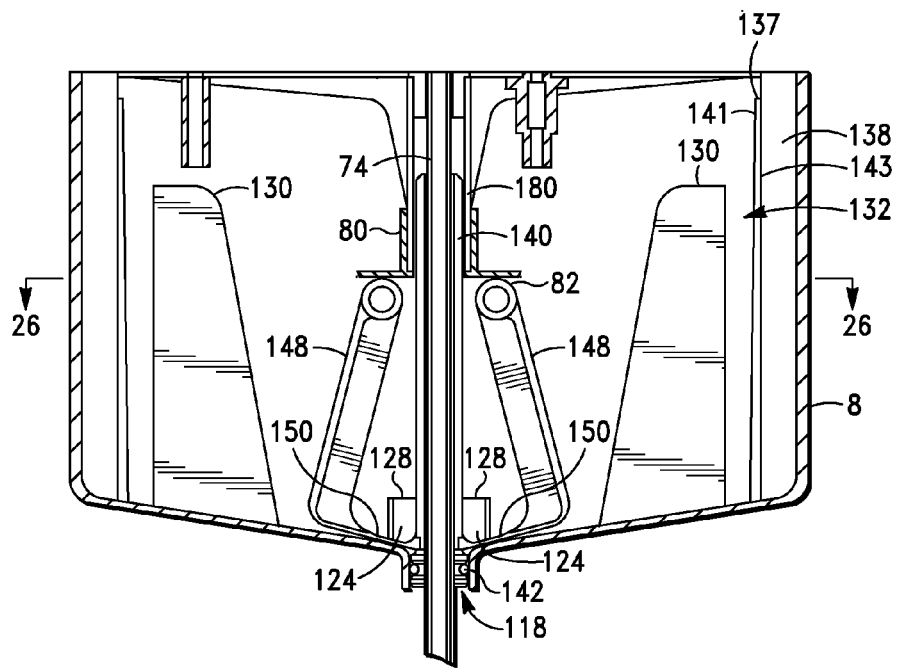
FIG. 25 is a cross-sectional view of the upper bucket and valve assembly of FIG. 4, taken along the central axis.

FIG. 25 is a cross-sectional view of the upper bucket and valve subassembly of FIG. 4, taken along the central axis, and FIG. 26 is a cross-sectional view of the upper bucket and valve assembly of FIG. 25, taken along the line 26-26. This is the view when blood is initially introduced into the top bucket 8. The arms 148 of the valve subassembly are in their initial upright position, with the central tube 140 positioned in the guide tube 80 and the upper end of each arm contacting the flange 82. The valve face 142 is in position in the valve seat 119 (FIG. 12) at the upper end of the central passageway 118, closing the passageway and preventing escape of blood. The flexible portions 150 of the arms 148 are positioned in the channels between the abutment plates 124 and 126, preventing rotation of the arms 148 about tube 74 during shipment and handling.

Figure 27:
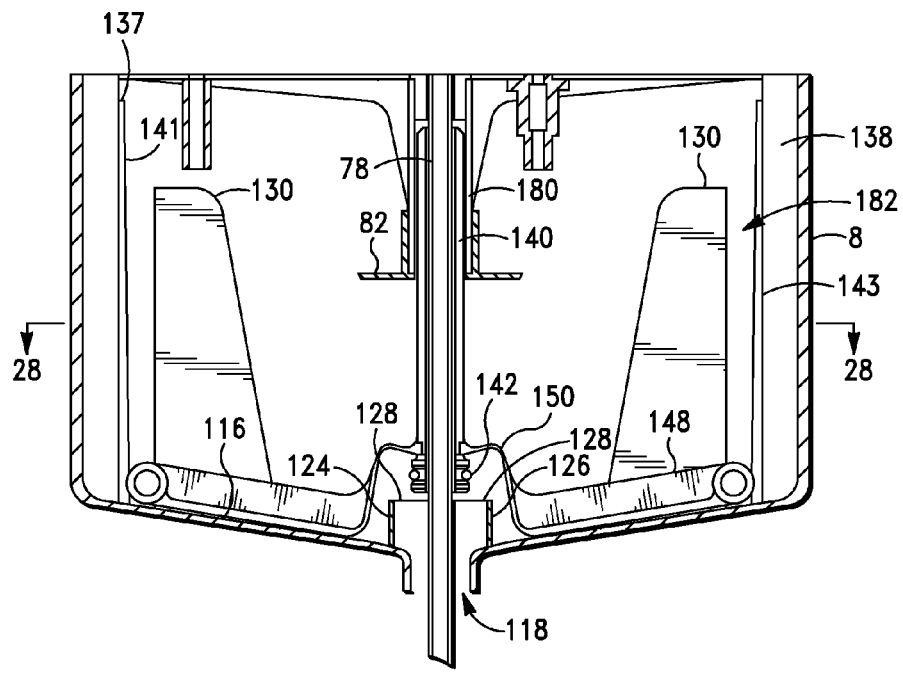
FIG. 27 is a cross-sectional view of the upper bucket and valve assembly of FIG. 4, after the centrifugal action of the spinning upper bucket has extended the arms of the valve assembly and opened the valve.
Figure 28:
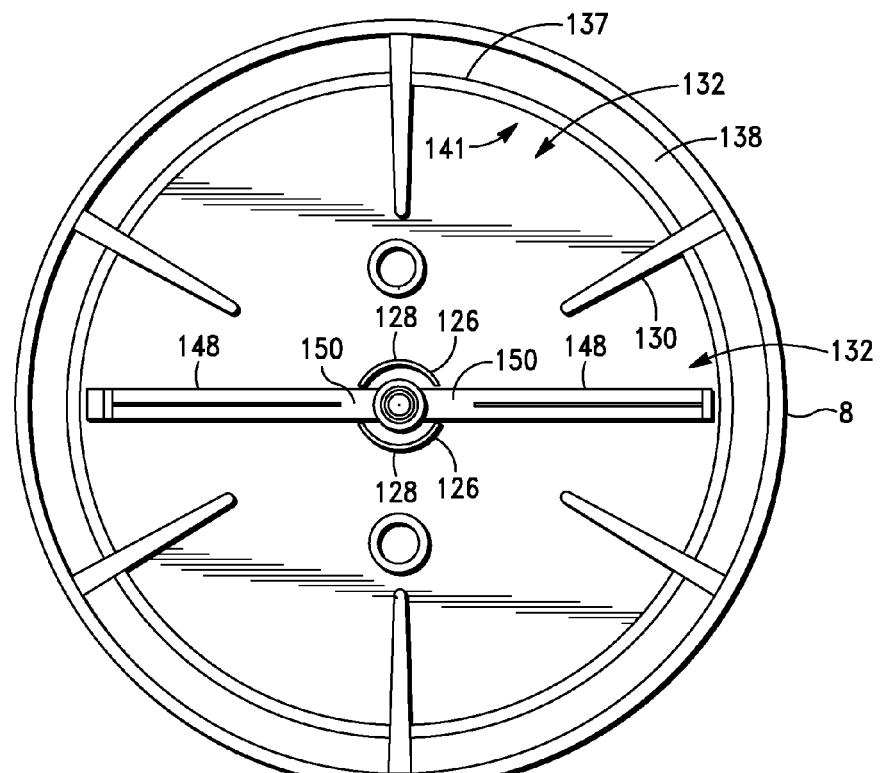
FIG. 28 is a cross-sectional view of the view of upper bucket and valve assembly of FIG. 27, taken along the line 28-28.

FIG. 27 is a cross-sectional view of the upper bucket and valve assembly of FIGS. 25 and 26, after the centrifugal action of the spinning upper bucket has extended the arms of the valve assembly and opened the valve, and FIG. 28 is a cross-sectional view of the view of upper bucket and valve assembly of FIG. 27, taken along the line 28-28. After the desired volume of patient blood has been introduced into the top bucket 8, the separation and concentration assembly is rotated around the tube 74 at a high speed, the centrifugal force created by this rotation causing the blood to flow outward where it can be distributed evenly by the separation plates into the separation zones 132. The centrifugal force pools the blood against the outer surface of the foam segments 138 where the more dense materials, such as erythrocytes, preferentially move into the foam, leaving behind less dense material, such as erythrocyte-free plasma which can also contain the less dense platelets.

Under the force of centrifugation, the valve arms 148 rotate outward until they contact the sloped floor 116. This action slides the valve central tube 140 upward to the upper portion of the guide cylinder 180, pulling the valve face 142 from the central passageway 118 and out of contact with the valve seat 119 to open the passageway 118. As the arms 148 rotate outward and the valve face 142 is lifted, the lower flexible ends 150 of the arms 148 are also pivoted upward from between the abutment plates 124 and 126, freeing the arms for rotation about the tube 74. Because the liquid is held against the foam segments 138 by centrifugal force, it does not flow through the open passageway 118.

Figure 29:
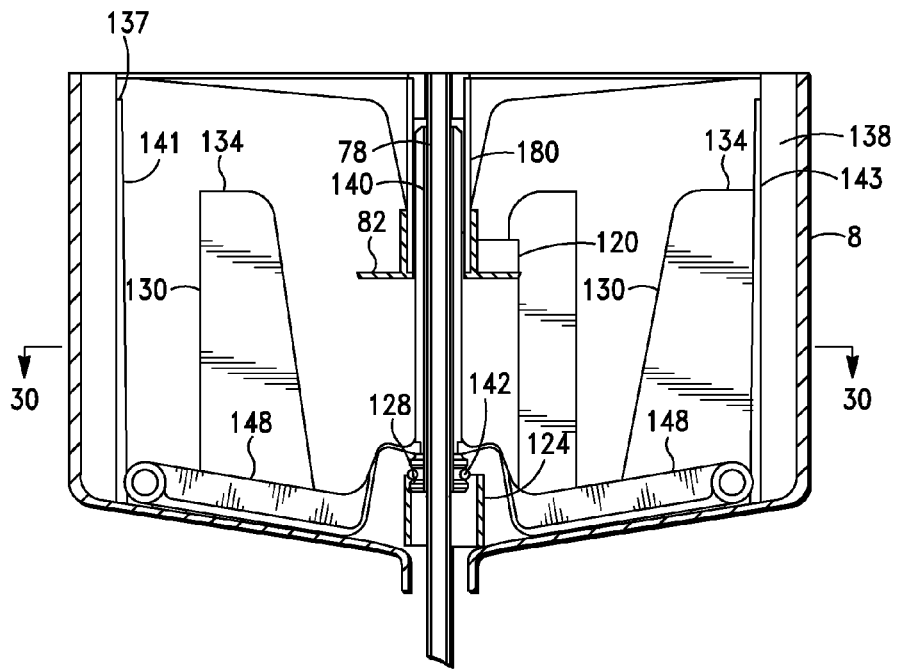
FIG. 29 is a cross-sectional view of the upper bucket and valve assembly of FIG. 27, after rotational displacement of the arms of the valve assembly.
Figure 30:
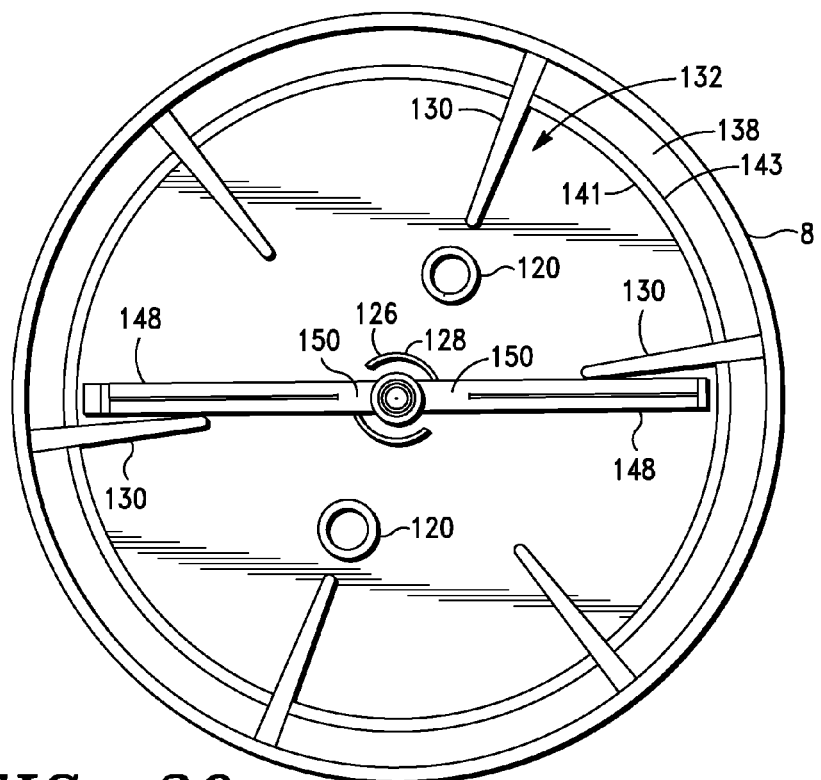
FIG. 30 is a cross-sectional view of the upper bucket and valve assembly of FIG. 29, taken along the line 30-30.

FIG. 29 is a cross-sectional view of the upper bucket and valve assembly of FIGS. 27 and 28, after rotational displacement of the arms of the valve assembly, and FIG. 30 is a cross-sectional view of the valve structure of FIG. 29, taken along the line 30-30. When the arms 148 are lifted from between the abutment plates and are freed from constraint by the abutment plates 124, rotational motion causes the arms 148 to rotate about the rigid tube 74. The rotation continues until one of the arms 148 contacts an adjacent separation plate 130 in its rotational path. This rotational displacement aligns the lower flexible ends 150 of the arms 148 above a portion of an abutment surface 128 of an abutment plate 124.

Figure 31:
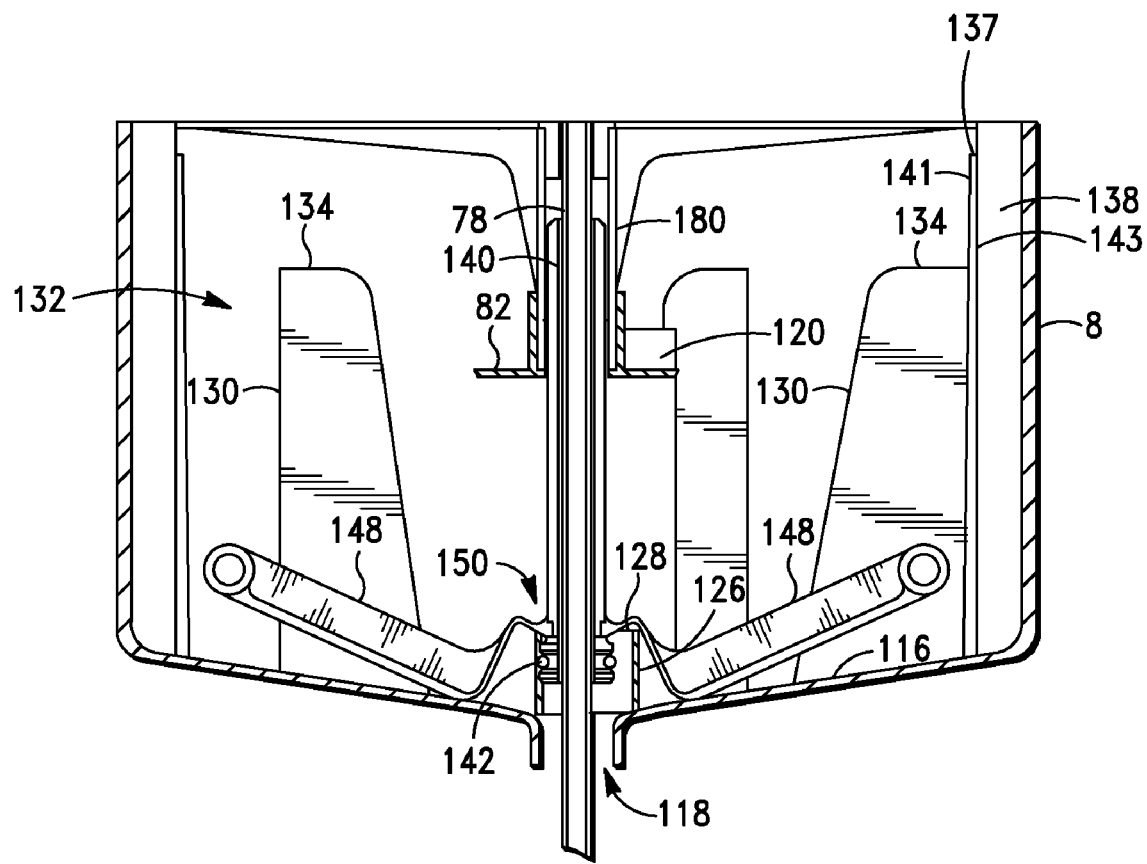
FIG. 31 is a cross-sectional view of the upper bucket and valve assembly of FIG. 29, after centrifugal separation has been completed.

FIG. 31 is a cross-sectional view of the upper bucket and valve assembly of FIGS. 29 and 30, after centrifugal separation has been completed and the rotation of the separation and concentration subassemblies is slowed or stopped. Under the force of gravity, the platelet-plasma mixture flows to the bottom of the tapered floor 116, down its sloped surface to the central passageway 118, and through the central passageway 118 to the basket subassembly 18 for concentration. The removal of the strong centrifugal action may permit the arms 148 to spring upward, causing the valve face 142 to move downward toward the central passageway 118. This movement is stopped when one or both flexible arm portions 150 contact an opposed abutment surface 128, leaving the central passageway open to the flow of the platelet-plasma mixture.

The operation of the device including the separation phase and concentrating phase of a material, such as whole blood, are described hereinafter in conjunction with FIGS. 32-36. Although the separation and concentration of whole blood are described in detail, other materials can also be separated and concentrated.

Figure 32:
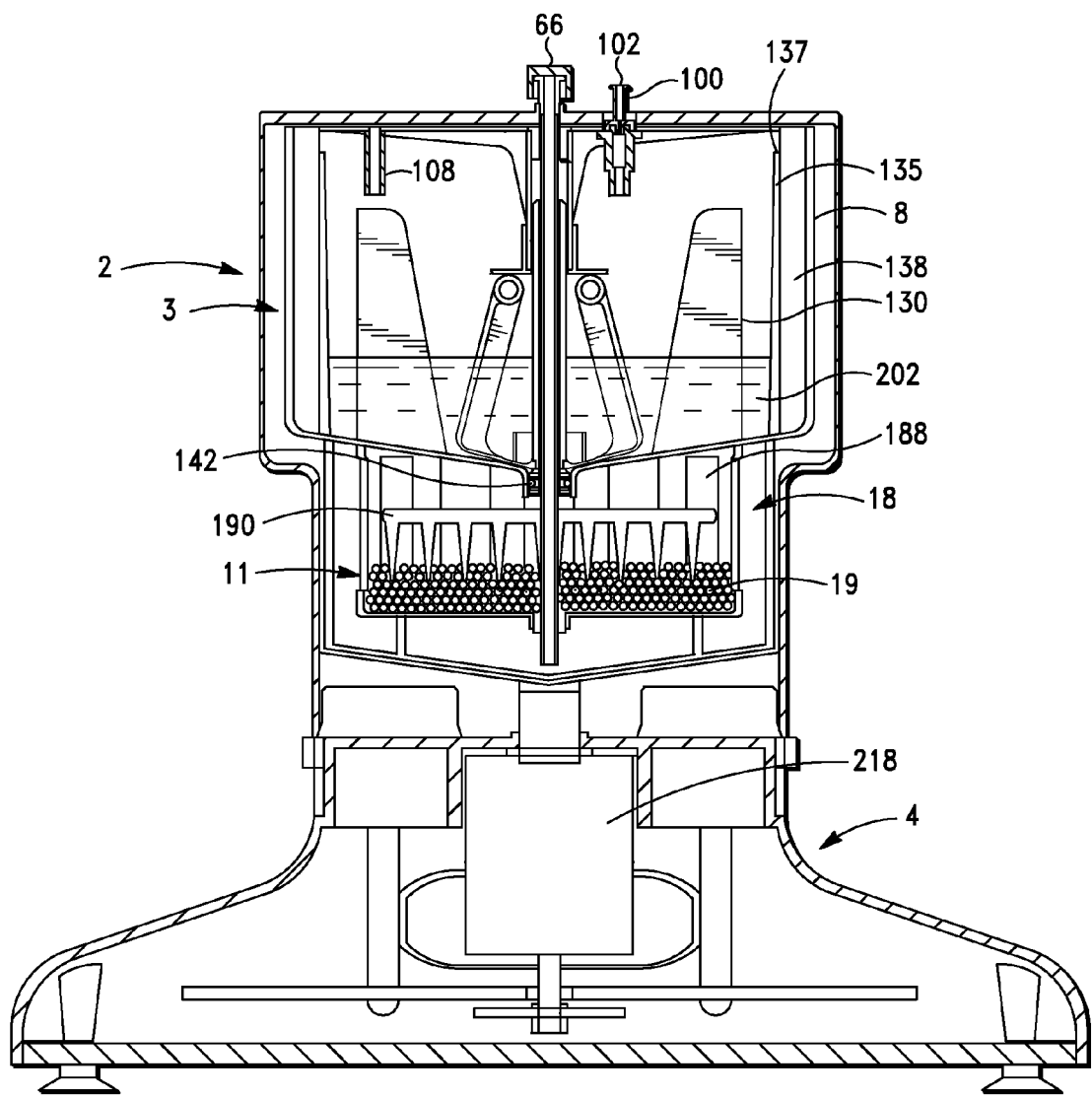
FIG. 32 is a cross-sectional view of the separation and concentration assembly of FIG. 1, after blood has been introduced into the separation chamber.

FIG. 32 is a cross-sectional view of the separation and concentration assemblies of FIG. 4, after blood 202 has been introduced into the separation assembly 3 through the tube 110 from a syringe secured to the Luer fitting 102. The upper tube 100 with the Luer fitting is then removed, unlocking the separation and concentration assemblies 3 and 11 for rotation. The blood flows into the bottom of the top bucket 8. Air displaced by the incoming liquid escapes through breathing tube 108. The valve face 142 is in a closed position, preventing escape of the blood from the bucket 8. The operation of the system is then initiated, and the motor 218 spins the separation and concentration assemblies together around the rigid tube 74.

Figure 33:
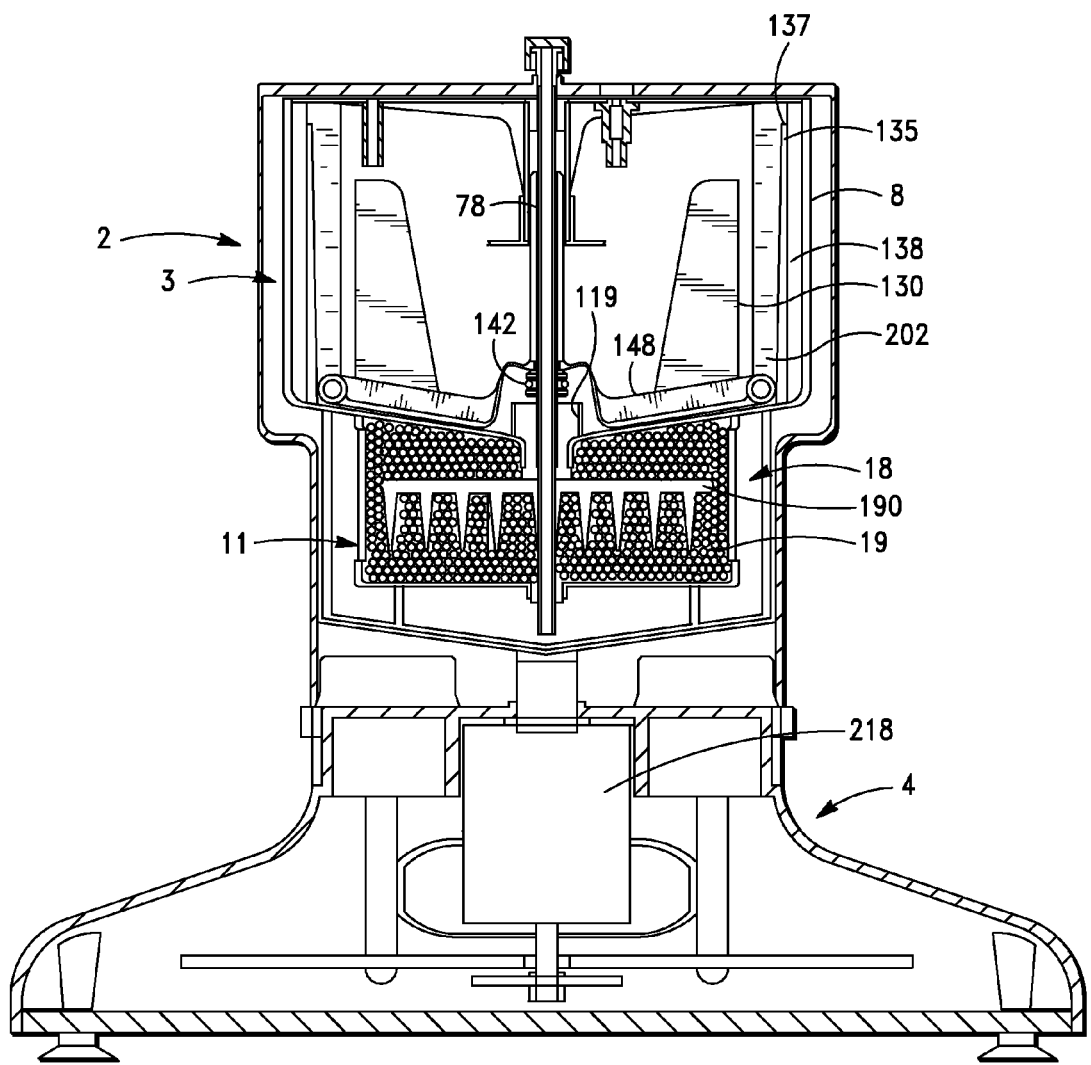
FIG. 33 is a cross-sectional view of the separation and concentration assembly of FIG. 32 as erythrocytes are separated from the plasma-platelet mixture during high speed centrifugation.

FIG. 33 is a cross-sectional view of the separation and concentration assemblies of FIG. 32 as erythrocytes are separated from the plasma-platelet mixture during high speed centrifugation. As the separation and concentration assemblies turn at a high speed, the blood is forced against the foam 138. The erythrocytes, being denser than other blood components, migrate into the pores and passageways of the foam. The valve subassembly opens the valve 142 as the centrifugal forces pivot the outer ends of the arms 148 away from the center, raising the valve face 142 face from valve seat 119 in the central passageway 118. However, as long as the high speed centrifugation continues, all of the liquid can be maintained against the foam. The centrifugal forces also force the hydrogel beads 19 radially outward against the outer screens 188 of the basket subassembly, out of contact with elements of the rake 190. Centrifugation is continued until a majority of the erythrocytes are completely trapped in the foam. Because any erythrocytes can weaken the gel product formed when the product is applied, the removal of a maximum proportion of the erythrocytes can be selected. The speed of centrifugation tends to separate erythrocytes from platelets, leaving a substantial portion of the platelets in the plasma while entrapping a majority of the erythrocytes in the foam.

Figure 34:
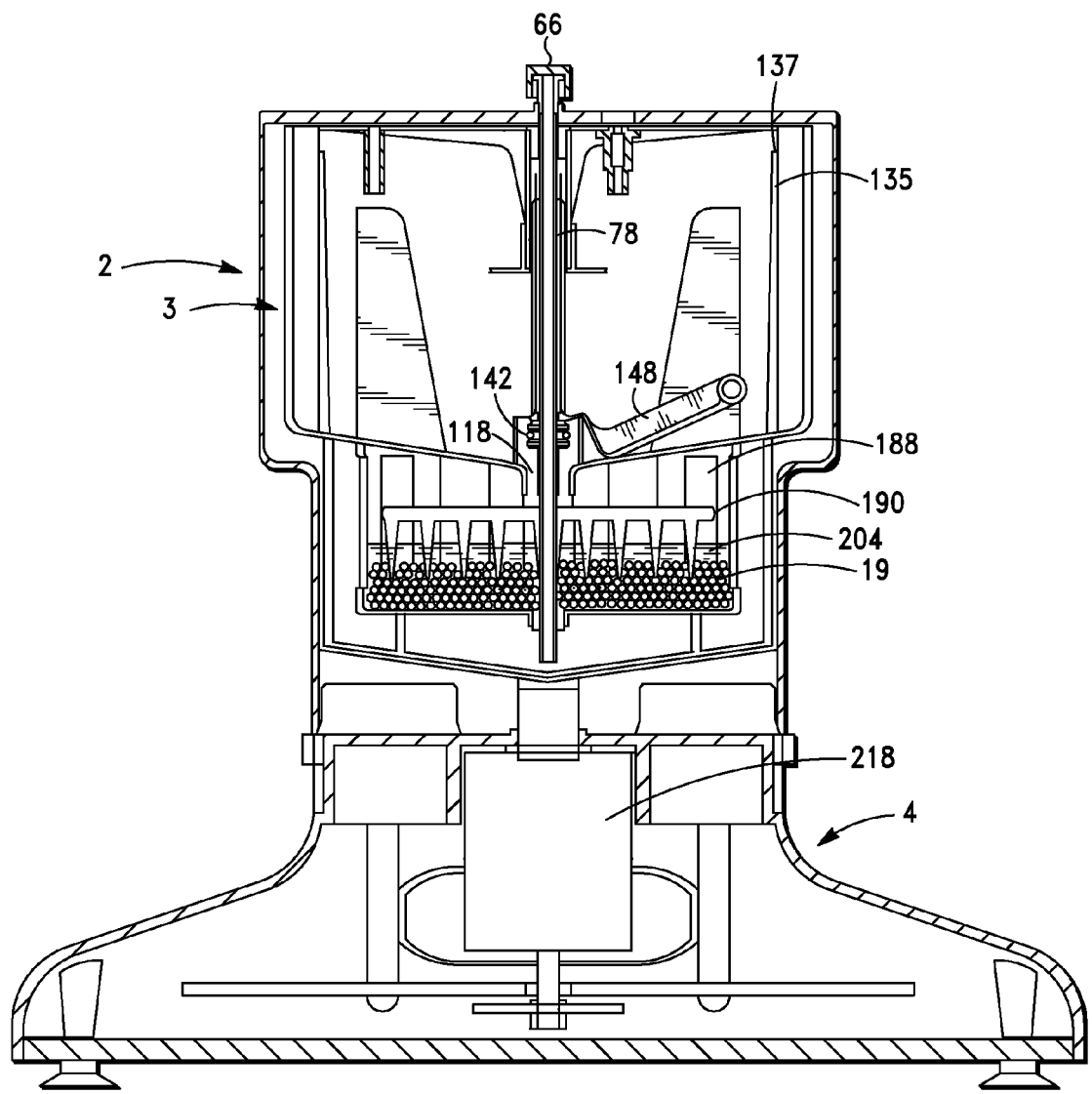
FIG. 34 is cross-sectional view of the separation and concentration assembly of FIG. 33, after platelet-plasma fraction has passed into the concentration chamber.

FIG. 34 is a cross-sectional view of the separation and concentration assembly of FIG. 33. After the spinning is slowed or stopped, the platelet-plasma fraction 204 flows to the bottom of the upper bucket 8 and down through the central passageway 118 into the basket subassembly 18 where it comes into contact with the desiccating hydrogel beads 19. These beads concentrate the plasma by absorbing water from the liquid. The separation and concentrating assemblies are then rotated at a slow speed by the motor 218, stirring the beads by moving them through the stationary spines 196 of the rake 190. Agitating the beads insures maximum contact of the beads surfaces with the plasma and reduces gel polarization that arises when the plasma thickens adjacent the bead surfaces. This desiccating phase is continued until the desired proportion of the water has been removed and the desired concentration of the plasma has been achieved.

Figure 35:
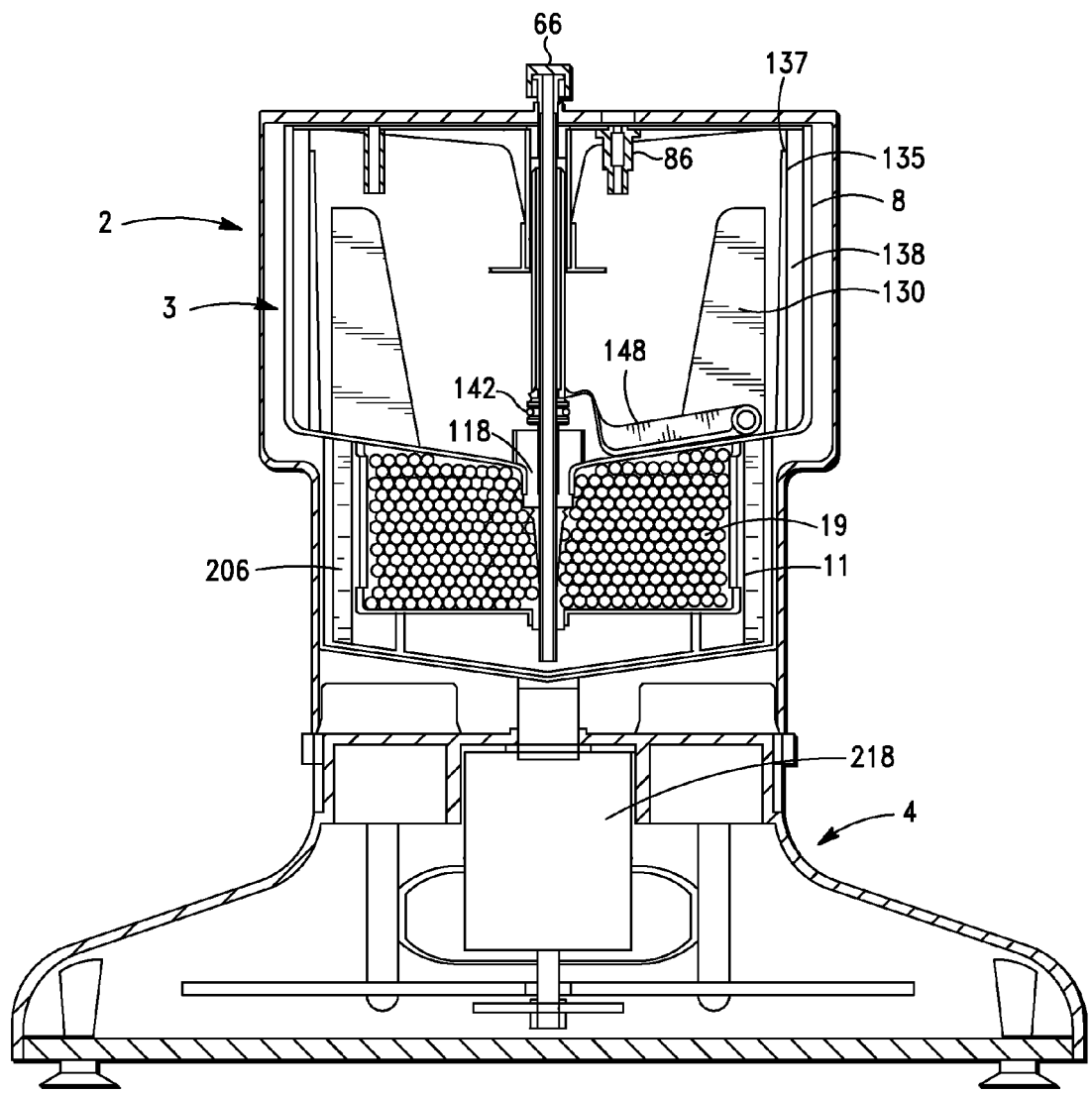
FIG. 35 is a cross-sectional view of the separation and concentration assembly of FIG. 34 at the beginning of the high speed centrifugation to separate the platelet-plasma concentrate from the hydrogel bead.

FIG. 35 is a cross-sectional view of the separation and concentration assembly of FIG. 34 at the beginning of high speed centrifugation separation of the platelet-plasma concentrate from the hydrogel beads. At this stage, removal and selected or maximum recovery of the platelet rich plasma concentrate 206 from the beads 19 is obtained. The separation and concentration assemblies are rapidly rotated by the motor 218 around the stationary tube 74, creating centrifugal forces that force the platelet rich plasma concentrate and the beads 19 against the screen elements 188 of the basket 18. The screen elements prevent escape of the beads 19 as the continuing centrifugal force causes the platelet enriched plasma concentrate to flow from the beads and through the screen. This high speed centrifugation is continued until a selected or maximum recovery of the platelet rich plasma is obtained.

The absorption of water by the hydrogel beads is accompanied by an increase in bead diameter, increasing the bead volume. If the increased bead volume causes the ends of the rake 190 to drag on beads packed on the screen surface, the rake can break along the break-away notches 200 (FIG. 19), and the rake fragments become mixed with the beads.

Figure 36:
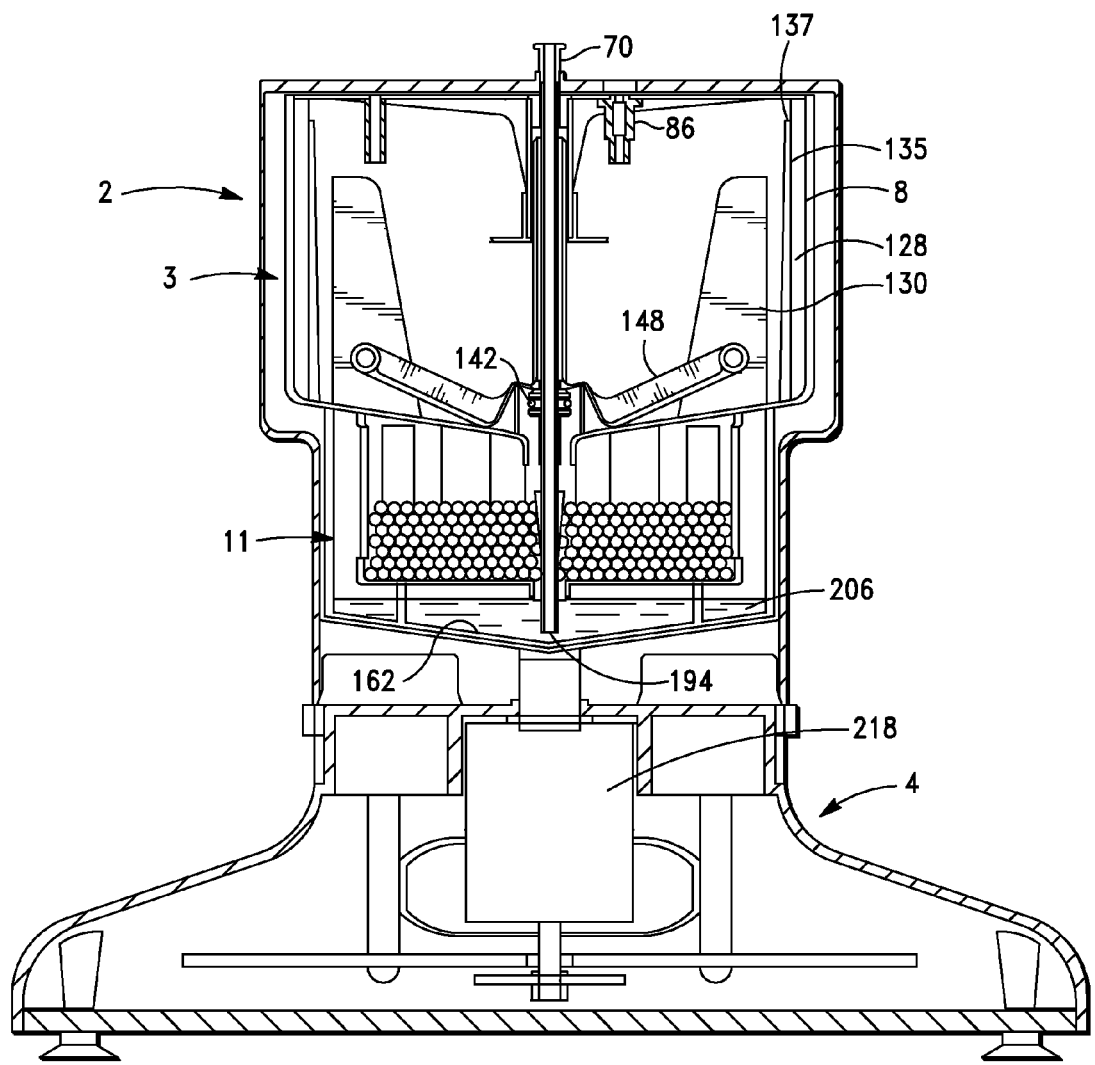
FIG. 36 is a cross a cross-sectional view of the separation and concentration assembly of FIG. 35 after platelet-plasma concentrate has collected in the platelet-plasma concentrate sump.

FIG. 36 is a cross-sectional view of the separation and concentration assembly of FIG. 35 after the high speed centrifugation has ended and the platelet-plasma concentrate has flowed into the platelet-plasma concentrate sump 162. The cap 66 has been removed, exposing Luer fitting 70 at the upper end of the tube 60. An applicator syringe (not shown) can be secured to the Luer fitting 70. The platelet-rich plasma concentrate is removed from the sump 162 by retracting the barrel of the applicator syringe, drawing platelet rich plasma concentrate up through the tubes 74 and 60 and into the syringe. Breathing tube 108 permits air to flow into the system to replace the volume of liquid removed by the syringe, thus preventing the creation of a partial vacuum in the system that would impede liquid removal.

Regarding the concentration factor, for maximum wound-healing, the platelet level can be maximized and high concentrate ion factors can be created. For homeostasis, plasma concentrations of about 3 to about 4 fold over anti-coagulated plasma levels are most effective. Concentrations below about 3 fold have an insufficient fibrinogen concentration. Concentrations higher than about 4 fold have excessive levels of total protein (principally albumin) which interferes with the fibrin gel structure. To obtain a preparation that maximizes haemostatic effectiveness while also providing improved (albeit perhaps less than maximal) wound-healing potential, a concentration range of about 3 to about 4 fold over anti-coagulated plasma levels may be selected. For applications where sealant activity is not desired, high concentrations may be selected.

Regarding erythrocyte levels, normal human hematocrits vary from about 37 percent or lower to about 52 percent for whole blood, measured after a very high speed spin. To achieve concentrations of about 3 fold or higher, some erythrocyte removal may be selected. However, the tensile strength of concentrated plasma gels diminish as the level of erythrocyte contamination increases. The concentration of erythrocytes in the final concentrate should be less than about 3 to about 5 percent to provide effective haemostatic properties. The separation and concentration device can be used to remove as much of the erythrocytes as is technically practical with the system, although trace contamination is acceptable. For applications where sealant activities are not desired, higher levels of erythrocytes can be maintained.

Regarding volume, both the depth filter and the beads reduce the liquid volumes being processed. Because of this volume loss, from about 14 to about 17 percent volume yields of effective haemostatic wound-healing product is generally obtained from average patient blood with the separation and concentration device. To make an effective product, the depth filter volume is selected to retain about 50 percent of the anti-coagulated blood (blood containing anticoagulant) and product about a 50 percent yield of PRP. The amount of the beads, in water absorption units, is selected to retain water equaling about 67 percent of the PRP volume.

Regarding accuracy, the amount of the depth filter and beads in each system is carefully selected to yield an optimum product. However, because of the wide range of hematocrit levels in patient populations, an approximate balance of components can be determined and selected.

If too much blood is added to the device, there is a greater chance that the product will have a substantial erythrocyte contamination, and the final product will be less concentrated than selected because the volume exceeds the practical capacity of the depth filter. Because the volume retained by the depth filter is about half the total volume of blood to be processed, if the volume of blood introduced into the device is too small, a substantially lower volume of PRP may be delivered to the beads. For example, if the blood volume is low by about 25 percent, this will result in about 50 percent of the desired volume being delivered to the beads. If the volume of PRP contacting the beads is low by 33 percent or more, no product will be recovered because the beads may absorb as much as about 67 percent or more of the targeted PRP volume. If the volume contacting the beads is short by about 17 percent, this may yield half of the desired volume of final product with twice the desired concentration (and hence of little value as a hemostat). In other words, a small error in the volume of blood introduced into the device is amplified into a large error in final product volume and concentration factor.

The systems can be designed to specifically match the hematocrit levels of the particular patient's blood to be processed. For a single optimized universal device, the device is optimized for the average patient blood, using fixed volumes of depth filter and blood, and a fixed bead water absorption capacity.

If it is selected to tolerate inaccuracy of introduced blood volume, the device can incorporate an overflow chamber as described in provisional patent application Ser. No. 60/654,718 filed Feb. 17, 2005 and U.S. patent application Ser. No. 11/342,761, filed on Jan. 30, 2006, the contents of which are hereby incorporated by reference.

EXAMPLE

Standard System Operation

Blood was processed with a device as shown and described in this application.

1) The initial spin was continued for 10 seconds at 250 rpm. This spin allows beads to be flung out into the cage under sufficiently low rpm that the initial imbalance does not generate excessive vibration. The outer ends of the rakes (the outermost tines) level the beads around the perimeter of the basket to balance the beads.

2) The erythrocytes were separated with the an erythrocyte separation spin of 3200 rpm for 90 seconds, packing the erythrocytes into the depth filter.

3) The PRP was concentrated by slowing the spin to 50 rpm for 45 seconds, draining PRP into the concentrator chamber and mixing the PRP with the beads.

4) The PRP concentrate was then removed from the beads by a final high-speed spin at 3200 rpm for 45 seconds.

The rates of acceleration and deceleration between stages were moderated to reduce vibration.

The process parameters were as follows:

| | |
|---|---|
| Start Volume | 150 cc |
| Retained by depth filter | 75 cc |
| Recovered concentrate | 23 cc |
| Platelet count | 3 fold increase over whole blood |
| Fibrinogen concentration | 2.8-3.2 fold increase over while blood |
| Erythrocytes in product | Undetected (less than 1%) |

The teachings herein are merely exemplary in nature and, thus, variations that do not depart from the gist of the teachings are intended to be within the scope of the teachings. Such variations are not to be regarded as a departure from the spirit and scope of the teachings.

What is claimed is:

1. A method for separating platelet rich plasma from a blood sample with a system comprising an inner wall having a top edge and a central axis surrounded by a depth filter having a capacity to receive all of the erythrocytes in the blood sample but insufficient to receive all of the plasma in the blood sample, an inner surface of the inner wall having an angle of at least about 0.2 degrees from the central axis of the inner wall, the method comprising the steps of:

a) spinning an inner cylinder about its central axis at a speed that centrifugally separates erythrocytes from plasma and platelets of the blood sample and causes the erythrocytes to collect against an inner surface of the depth filter;

b) continuing spinning for a time sufficient to allow substantially all of the erythrocytes to flow up the inner surface and over the top edge into the depth filter, leaving platelet enriched plasma behind in the inner cylinder; and c) slowing or discontinuing the spinning to permit the platelet enriched plasma to flow to the bottom of the inner cylinder.

2. The method of claim 1, further comprising:

segmenting the inner surface of the inner wall by radially extending plates to form separation zones;

balancing distribution of the blood in the separation zones with the plates during rotation of the inner cylinder, thereby reducing vibration and erythrocyte displacement from the depth filter.

3. The method of claim 1 wherein a rotational speed of the inner cylinder is accelerated to centrifugal speeds at a rate that allows balanced distribution of blood in separation zones, and after the centrifuging is complete, the rotation speed of the inner cylinder is decelerated to below centrifugal speeds at a rate that allows balanced distribution of the blood sample in the separation zones, thereby reducing vibration and erythrocyte displacement from the depth filter.

4. The method of claim 1 further comprising concentrating the platelet enriched plasma by contacting the platelet enriched plasma with desiccating beads in a concentration chamber while the beads are agitated with a rake to form a platelet rich plasma concentrate.

5. The method of claim 4 wherein the concentration chamber includes an outer screened cylinder for the desiccating beads, and the platelet rich plasma concentrate is separated from the beads by rotating the concentrating chamber about its central axis at a speed that separates platelet rich plasma concentrate from the beads.

6. The method of claim 1 further comprising retaining at least about 85 volume percent of a hematocrit value of the blood and less than a major portion of the platelet enriched plasma remaining after the erythrocyte separation.

7. The method of claim 1 further comprising retaining at least about 97 volume percent of a hematocrit value of the blood and less than a major portion of the platelet enriched plasma remaining after the erythrocyte separation.

8. The method of claim 1 further comprising retaining at least about 99 volume percent of a hematocrit value of the blood sample and less than a major portion of the platelet enriched plasma remaining after the erythrocyte separation.

9. The method of claim 1 further comprising retaining at least about 100 volume percent of a hematocrit value of the blood and less than a major portion of the platelet enriched plasma remaining after the erythrocyte separation.

10. The method of claim 9 further comprising retaining less than a significant portion of the enriched plasma remaining after the erythrocyte separation.

11. A method for separating platelet rich plasma from a blood sample with a system comprising an inner wall having a top edge surrounding a central axis, a depth filter having a capacity to receive erythrocytes from the blood sample, an inner surface of the inner wall having an angle from the central axis, the method comprising:

a) spinning an inner cylinder about the central axis at a speed that centrifugally separates erythrocytes from the blood sample;

b) continuing spinning for a time sufficient to allow a selected portion of the erythrocytes to move up the inner surface of the inner wall and over a top edge of the inner wall into the depth filter, leaving platelet enriched plasma in the inner cylinder; and c) slowing or discontinuing the spinning to permit the platelet enriched plasma to flow to a bottom of the inner cylinder.

12. The method of claim 11, further comprising:

balancing distribution of the blood during the spinning of the inner cylinder in a plurality of separation zones thereby reducing vibration and erythrocyte displacement from the depth filter, wherein the separation zones are defined by plates radially extending from the inner wall.

13. The method of claim 12, further comprising:

increasing a speed of spinning of the inner cylinder at a rate that allows balanced distribution of blood in the separation zones; and wherein slowing or discontinuing the spinning includes decelerating the inner cylinder at a rate that allows balanced distribution of the blood sample in the separation zones.

14. The method of claim 11, further comprising:

concentrating the platelet rich plasma by contacting the platelet rich plasma with desiccating beads in a concentration chamber while the beads are agitated with a rake to form a platelet rich plasma concentrate.

15. The method of claim 14 wherein the concentration chamber includes an outer screened cylinder to contain the desiccating beads, and the platelet rich plasma concentrate is separated from the beads by rotating the concentrating chamber about its central axis at a speed that separates platelet rich plasma concentrate from the beads.

16. The method of claim 11, further comprising:

retaining at least about 85 volume percent of a hematocrit value of the blood and less than a major portion of the erythrocyte free platelet enriched plasma remaining after the erythrocyte separation.

17. The method of claim 11, further comprising:

retaining at least about 97 volume percent of a hematocrit value of the blood and less than a major portion of the platelet enriched plasma remaining after the erythrocyte separation.

18. The method of claim 11 further comprising:

retaining less than a significant portion of the platelet enriched plasma remaining after the erythrocyte separation.

19. A method for separating at least erythrocytes from a blood sample the method comprising:

placing the blood sample in a system having a central axis surrounded by an inner wall extending to a top edge and the inner wall having an inner surface having an angle from the central axis, the system further having a depth filter to receive erythrocytes from the blood sample;

accelerating the system to spin around the central axis;

continuing spinning of the system for a time sufficient to allow a selected portion of the erythrocytes to move up the inner surface of the inner wall and over the top edge of the inner wall into the depth filter, leaving platelet enriched plasma in an inner cylinder defined at least in part by the inner wall; and decelerating or discontinuing the spinning of the system to permit the platelet enriched plasma to collect in the system.

20. The method of claim 19, further comprising:

balancing distribution of the blood during the spinning of the system in a plurality of separation zones thereby reducing vibration and erythrocyte displacement from the depth filter, wherein the separation zones are defined by plates radially extending from the inner wall.

21. The method of claim 19, further comprising:

concentrating the platelet enriched plasma by contacting the platelet enriched plasma with desiccating beads in a rotating concentration chamber while the beads are agitated with a rake to form a platelet rich plasma concentrate.

22. The method of claim 21, wherein the concentration chamber includes an outer screened cylinder to contain the desiccating beads, and the platelet rich plasma concentrate is separated from the beads by rotating the concentrating chamber about its central axis at a speed that separates platelet rich plasma concentrate from the beads.

* * * * *